US005747300A

United States Patent [19]
Nishimoto et al.

[11] Patent Number: 5,747,300
[45] Date of Patent: *May 5, 1998

[54] TREHALOSE AND ITS PRODUCTION AND USE

[75] Inventors: Tomoyuki Nishimoto; Hiroto Chaen; Toshiyuki Sugimoto; Toshio Miyake, all of Okayama, Japan

[73] Assignee: Kabushiki Kaisha Hayashibara Seibutsu Kagaku Kenkyujo, Okayama, Japan

[*] Notice: The term of this patent shall not extend beyond the expiration date of Pat. No. 5,538,883.

[21] Appl. No.: 620,172

[22] Filed: Mar. 22, 1996

Related U.S. Application Data

[62] Division of Ser. No. 503,426, Jul. 17, 1995, abandoned.

[30] Foreign Application Priority Data

Jul. 19, 1994 [JP] Japan .................................. 6-187901
Apr. 24, 1995 [JP] Japan .................................. 7-120387

[51] Int. Cl.$^6$ .................................................. C12P 19/04
[52] U.S. Cl. .......................... 435/101; 435/96; 435/98; 435/170; 435/874
[58] Field of Search .................. 435/101, 170, 435/874, 96, 98

[56] References Cited

U.S. PATENT DOCUMENTS

| | | |
|---|---|---|
| 3,795,584 | 3/1974 | Mitsuhashi et al. . |
| 3,832,285 | 8/1974 | Kurimoto et al. . |
| 4,032,403 | 6/1977 | Sakai et al. . |
| 4,521,252 | 6/1985 | Miyake et al. . |
| 4,594,322 | 6/1986 | Thompson et al. . |
| 5,169,767 | 12/1992 | Matsuura et al. . |
| 5,538,883 | 7/1996 | Nishimoto et al. ................... 435/200 |

FOREIGN PATENT DOCUMENTS

| | | |
|---|---|---|
| 0257535 | 3/1988 | European Pat. Off. . |
| 0302838 | 2/1989 | European Pat. Off. . |
| 0327391 | 8/1989 | European Pat. Off. . |
| 0447125 | 9/1991 | European Pat. Off. . |
| 0606753 | 7/1994 | European Pat. Off. . |
| 1958014 | 6/1970 | Germany . |
| 47-013089 | 4/1972 | Japan . |
| 50-154485 | 12/1975 | Japan . |
| 54-003938 | 2/1979 | Japan . |
| 56-11437 | 3/1981 | Japan . |
| 56-017078 | 4/1981 | Japan . |
| 56-028153 | 6/1981 | Japan . |
| 56-028154 | 6/1981 | Japan . |
| 57-003356 | 1/1982 | Japan . |
| 58-023799 | 2/1983 | Japan . |
| 58-072598 | 4/1983 | Japan . |
| 58-216695 | 12/1983 | Japan . |
| 63-42696 | 2/1988 | Japan . |
| 64-34296 | 2/1989 | Japan . |
| 4281795 | 10/1992 | Japan . |
| 2106912 | 4/1983 | United Kingdom . |
| 9117255 | 11/1991 | WIPO . |
| 9203565 | 3/1992 | WIPO . |

OTHER PUBLICATIONS

Ikeda et al, Lipase–Catalyzed Acylation of Sugars Solubilized in Hydrophobic Solvents By Complexion; Biotechnology and Bioengineering, vol. 42, pp. 788–791 (1993).

R.A. Rastall, et al, Synthesis of Oligosaccharides By Reversal of a Funal β–Glucanase; Biotechnology Letters, vol. 14, No. 5, May 1992, pp. 373–378.

I. Schick et al, Coenzyme–Independent Enzymatic Syntheisis of α,α–Trehalose; Biochemical Engineering–Stuttgart, pp. 126–129, 1991.

Murao et al, Enzymatic Synthesis of Trehalose From Maltose, Agric. Biol. Chem. 49 (7), 2113–2118, 1985.

B. Toussaint et al, Reactions of Reversion Occuring With the Trichoderma Reesei CL–847 Cellulase System; Biotechnology Letters, vol. 12, No. 8, pp. 587–592 (1990).

Suzuki et al, Pimelobacter Gen. Nov., A New Genus of Coryneform Bacteria With LL–Diaminopimelic Acid in the Cell Wall; Journal of General Applied Microbiology, vol. 29, pp. 59–71, 1983.

Bergey's Manual of Systematic Bacteriology, vol. 1, pp. 186–199.

Bergey's Manual of Systematic Bacteriology, vol. 2, pp. 11265, 1292, 1300, 1482–1485.

Advances in Carbohydrate Chemistry, vol. 18, 1963, pp. 201–225.

Hoelzle et al, Increased Accumulation of Trehalose in Rhizobia Cultured Under 1% Oxygen; Applied and Environmental Microbiology, vol. 56, No. 10, pp. 3213–3215, 1990.

Atsuji et al, Journal of Clinical Nutrition, vol. 41, No. 2, pp. 200–208, 1972.

Kibayashi, Food Chemical, No. 8, pp. 67–72, 1992.

*Primary Examiner*—Herbert J. Lilling
*Attorney, Agent, or Firm*—Browdy and Neimark

[57] ABSTRACT

Microorganisms which are able to produce maltose/trehalose conversion enzyme, a novel enzyme, are cultivated in nutrient culture media with malose. During the cultivation, the microorganisms readily convert maltose into trehalose to accumulate trehalose in the cultures which yield saccharide mixtures with high trehalose contents when separated from insoluble substances. Removal of contaminant saccharides and subsequent crystallization readily yield trehalose in crystal-line trehalose hydrate or anhydrous crystalline form. The trehalose and saccharide mixture containing the same commonly bear desirable properties including mild sweetness and superior stability which render them very useful in a variety of compositions including food products, cosmetics and medicines.

12 Claims, 12 Drawing Sheets

TREHALOSE AND ITS PRODUCTION AND USE

This is a division of parent application Ser. No. 08/503,426 filed Jul. 17, 1995 now abandoned.

BACKGROUND OF THE INVENTION

1. Field of the Invention

The present invention relates to trehalose and its production and use, in particular, to trehalose or saccharide containing the same which is obtainable by cultivating in a nutrient culture medium with maltose a microorganism capable of producing maltose/trehalose conversion enzyme, as well as to a process to produce the same and use thereof.

2. Description of the Prior Art

Trehalose (alpha,alpha-trehalose) has been known from ancient times as non-reducing saccharide composed of glucose, and as described in *Advances in Carbohydrate Chemistry*, published by Academic Press Inc., New York, N.Y., U.S.A., Vol.18, pp.201–225 (1963) and *Applied and Environmental Microbiology*, Vol.56, pp.3,213–3,215 (1990), its trace but extensive distribution is found in microorganisms, mushrooms and insects. Since as is trehalose, non-reducing saccharides cause no aminocarbonyl reactions with substances bearing amino groups such as amino acids and proteins and therefore neither deteriorate nor alter them, the saccharides have been deemed to be useful in utilizing and processing such substances with no fears of their browning and deterioration: Thus establishment of processes which would enable their industrial-scale production has been in great expectation.

There have been known several processes to produce trehalose, for example, those using microorganism cells as disclosed in Japanese Patent Kokai No.154,485/75 and those converting maltose by combination of maltose phosphorylase and trehalose phosphorylase as disclosed in Japanese Patent Kokai No.216,695/83. The former process using microorganism cells is however inadequate for industrial-scale process because the trehalose content in microorganism cells as starting material is generally low, i.e. less than 15 w/w % (the percentages appeared hereinafter mean "w/w %" unless specified otherwise), and the extraction and purification steps for trehalose are very complicated. While the latter process using maltose phosphorylase and trehalose phosphorylase has not been realized in industrial scale due to the demerits that both enzymes commonly act via glucose-1-phosphate and this hinders elevated concentrations for substrates, that the yield for trehalose is low because both enzymes irreversibly act in the same reaction system, and further that such reaction system is very difficult to stably maintain and smoothly proceed.

In connection with this, *Gekkan Food Chemical (Monthly Food Chemical)*, "Recent Aspects and Issues in Utilization and Development of Starch", August, pp.67–72 (1992) comments in the corner of "Oligosaccharides" that although trehalose would have very extensive uses, its enzymatic production using any direct saccharide-transferring or hydrolyzing reactions has been deemed to be scientifically impossible at the present time, confirming that the production of trehalose from starch as material using enzymatic reactions has been deemed to be scientifically impossible.

While it is known that partial starch hydrolysates, for example, liquefied starch, dextrins and maltooligosaccharides which are all produced from starch, generally exhibit reducing powers due to the reducing end groups in their molecules. Such a partial starch hydrolysate will be designated as "reducing partial starch hydrolysate" in this specification. The reducing powers of reducing partial starch hydrolysates on dry solid basis are usually expressed by "Dextrose Equivalent" or "DE". Also is known that reducing partial starch hydrolysates with higher DE values, which are generally small molecules, exhibit low viscosities and strong sweetening powers, as well as high reactivities to substances with amino groups such as amino acids and proteins, which cause the aminocarbonyl reaction leading to browning, unpleasant smell and deterioration.

The characteristics of reducing partial starch hydrolysates vary dependently on the magnitudes of their DE and therefore the relationship between particular reducing partial starch hydrolysates and their DE values is very important. It has been however believed in the art to be impossible to cut off this relationship.

The sole method to cut off the relationship is to change reducing partial starch hydrolysates into non-reducing saccharides, for example, by converting their reducing groups into alcohol groups by high-pressure hydrogenation. This method however needs high-pressure autoclaves, safety facilities and careful control to prevent disasters, as well as consuming large amounts of hydrogen and energy. Further the obtained saccharide alcohols differ from reducing partial starch hydrolysates in the point that reducing partial starch hydrolysates consist of glucose moieties, while the saccharide alcohols consist of glucose and sorbitol and this may cause transient indigestion and diarrhea. Thus it has been in great demand to establish any methods by which the reducing powers of reducing partial starch hydrolysates are decreased or even eliminated without changing glucose moieties which compose reducing starch hydrolysates.

To solve these, the present inventors disclose in Japanese Patent Application No.144,092/94 a novel enzyme (referred to as "maltose/trehalose conversion enzyme" hereinafter) which is capable of converting maltose into trehalose, thus establishing a process to produce trehalose or saccharide containing the same from maltose using this maltose/trehalose conversion enzyme.

It was however found later that, unfavorably, such a process needed an extended time for cultivation of microorganisms to produce enzymes, recovery of the enzymes and enzymatic reaction to convert maltose into trehalose. Thus it is in great demand to establish any processes which would be more readily feasible in the production of trehalose from maltose with less complicated steps including those for preparation of enzymes.

SUMMARY OF THE INVENTION

The present invention is to establish a novel process which would readily yield trehalose from maltose with a shortened processing time, as well as to provide the use thereof.

To solve these objects, the present inventors energetically investigated the cultivation of microorganisms capable of producing maltose/trehalose conversion enzyme and also the production of the enzyme therefrom. As the result, the present inventors found that the microorganisms produced the enzyme in an early stage of cultivation, as well as that trehalose was readily formed and accumulated by incorporating maltose in nutrient culture media during cultivation. The present inventors accomplished this invention.

More particularly, the present invention is to establish trehalose or saccharide containing the same by cultivating in a nutrient culture medium with maltose a microorganism capable of producing maltose/trehalose conversion enzyme.

as well as to establish a process to produce the same and their use. It was found that in the present invention the preferred maltose preparations were those which were obtainable by subjecting a liquefied starch to either beta-amylase or to beta-amylase and starch-debranching enzyme, as well as that the use of microorganisms capable of producing maltose/trehalose conversion enzyme was very favorable with respect to production of trehalose. The trehalose or saccharide containing the same thus obtained can be favorably used in a variety of compositions including food products, cosmetics and medicines due to their elevated stability and handleability.

DETAILED DESCRIPTION OF THE INVENTION

Figure 1:
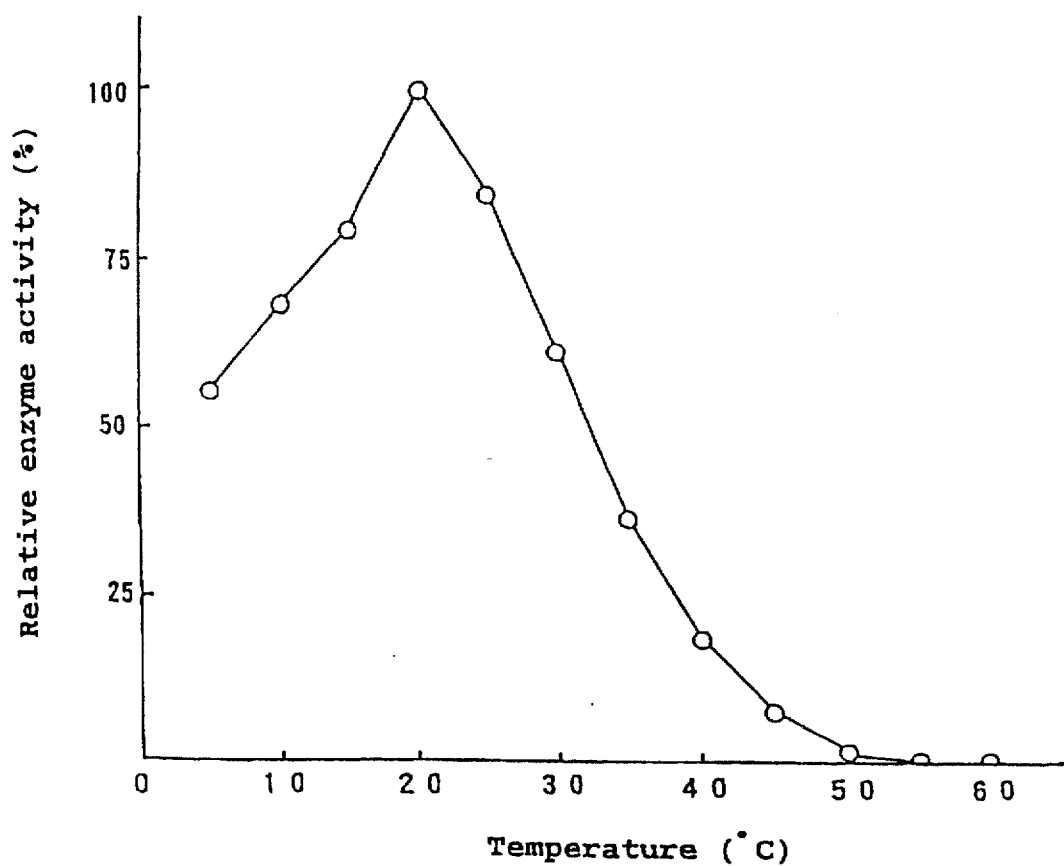
FIG. 1 shows the effect of temperature on the activity of the maltose/trehalose conversion enzyme derived from Pimelobacter species R48.

The microorganisms capable of producing maltose/trehalose conversion enzyme feasible in the present invention are those which produce enzymes capable of converting maltose into trehalose: Examples of such an enzyme include those derived from microorganisms of the genera Pimelobacter, Pseudomonas and Thermus which are disclosed in Japanese Patent Application No.144,092/94.

Nutrient culture media to be used in the cultivation of such a microorganism are those which contain maltose as substrate for the formation of trehalose and where the microorganism can grow and produce maltose/trehalose conversion enzyme. If necessary, one can arbitrarily use in combination other carbon sources including saccharides, for example, glucose, fructose, lactose, sucrose, mannitol, sorbitol and molasses, organic acids such as citric acid and succinic acid and their salts. Preferred concentrations for maltose in culture media are 20 w/v % or less, desirably, 15 w/v % or less, more desirably, about 5–10 w/v %. Examples of nitrogen sources are inorganic salts such as ammonium salts and nitrates and organic nitrogen compounds such as urea, corn steep liquor, casein, pepton, yeast extract and meat extract. Example of minerals are calcium salts, magnesium salts, potassium salts, sodium salts, phosphates, manganese salts, zinc salts, iron salts, copper salts, molybdenum salts and cabalt salts. If necessary, amino acids and vitamins can be arbitrarily used.

Cultivation is usually carried out under aerobic conditions where the microorganisms can grow, usually, at 4°–80° C., desirably, 20°–75° C. and at pH5–9, desirably, pH6–8.5. Cultivation time is set to a level where microorganisms can proliferate, for example, 10–100 hours. There are provided no special limitations in the oxygen concentration in cultures but preferred levels are usually 0.5–20 ppm. For this purpose, one can control aeration, stir, supplement oxygen and/or elevate the pressure in fermenters. Cultivation can be carried out in batch, continuous or semicontinuous manner.

Thus trehalose can be formed and accumulated in cultures by cultivating in a nutrient culture medium with maltose a microorganism capable of producing maltose/trehalose conversion enzyme. It is favorable to supplement or add in nutrient culture media during cultivation a separately prepared maltose/trehalose conversion enzyme, surface-active agent such as anion or non-ionic surface-active agent and/or lytic enzyme such as lysozyme in order to accelerate the formation of trehalose. The trehalose formed and accumulated in this manner is present in a liquid part which can be obtained by removing insoluble substances.

Cultures which contain trehalose are first prepared into cell-free liquids by conventional solid/liquid separation methods, for example, filtration and centrifugal separation and the liquids are then concentrated, decolored with activated carbon, deionized with ion exchanges of H- and OH-forms and further concentrated in conventional manner into syrup products. These products may be further dried into powder. If necessary, it is favorable in the production of trehalose or saccharide containing the same to apply whole cultures to membrane filters such as plain filters or hollow fibers to remove both cells and soluble polymers such as proteins and nucleic acids, or to remove first insoluble substances by centrifugal separation, then soluble polymers by membrane filters, prior to concentrating, decoloring and deionizing for purification.

Next the maltose/trehalose conversion enzyme which is involved in the formation of trehalose according to the present invention will be explained. Enzymatic activities are found in both cells and supernatants of cultures and therefore one can recover them as crude enzyme preparation or use whole cultures intact as crude enzyme preparation. To remove cells from cultures, conventional solid/liquid separation methods are employed. For example, one can arbitrarily choose a method where cultures are subjected to centrifugal separation, another method where cultures are separated by filtration using precoated filters, and still another method where cultures are separated by membrane filtration using plain membranes and hollow fibers. Cell-free liquids can be used intact as crude enzyme preparation but are usually concentrated prior to use. Concentration can be carried out, for example, by ammonium sulfate precipitation method, acetone/alcohol precipitation method and membrane concentration using plain membranes and hollow fibers.

Cell-free liquids and their concentrates can be immobilized in conventional manner. For this purpose, for example, binding to ion exchanges, covalent attachment or adsorption to resins and membranes and entrapment using polymers are employed. Cells, which have been separated from cultures, are used intact as crude enzyme preparation or immobilized prior to use. For example, cells are first mixed with sodium arginate, then dropped and gelatinized in calcium chloride solution into granular form. The granules may be further treated with polyethyleneimine or glutaraldehyde. One can extract enzymes from cells and use the extract as crude enzyme liquid. For example, cells are subjected first to ultrasonical disruption, mechanical disruption using glass beads and aluminum or French press disruption for extraction of enzymes, then to centrifugal separation or membrane filtration, thus obtaining a transparent crude enzyme liquid.

Such an enzyme liquid is used intact or further purified in conventional manner prior to use. For example, a crude enzyme preparation from culture which has been subjected to salting out by ammonium sulfate and concentration is first dialyzed, then purified on anion exchange column chromatography using "DEAE TOYOPEARL", hydrophobic column chromatography using "BUTYL TOYOPEARL" and gel filtration chromatography using "TOYOPEARL HW-55", all of which are products of Tosoh Corp., Tokyo, Japan, thus obtaining an electrophoretically homogenous enzyme preparation.

The maltose/trehalose conversion enzymes thus obtained generally bear the following physicochemical properties:

(1) Action
Capable of converting maltose into trehalose, as well as of converting trehalose into maltose.

(2) Molecular weight
About 57,000–120,000 daltons on SDS-gel electrophoresis.

(3) Isoelectric point
About pI3.8–5.1 on Ampholine electrophoresis.

(4) Inhibition of activity
Inhibited by 1 mM $Cu^{2+}$, $Hg^{2+}$ and 50 mM Tris-HCl buffer.

(5) Origin
Enzymes produced by microorganisms.

Several enzymes derived from different microorganisms are as illustrated below:

Maltose/trehalose conversion enzyme derived from Pimelobacter species R48

(1) Action
Capable of converting maltose into trehalose, as well as of converting trehalose into maltose. Forming from one mole of maltose or trehalose about one mole of trehalose or maltose respectively.

(2) Molecular weight
About 57,000–67,000 daltons on SDS-gel electrophoresis.

(3) Isoelectric point
About pI4.1–5.1 on Ampholine electrophoresis.

(4) Inhibition of activity
Inhibited by 1 mM $Cu^{2+}$, $Hg^{2+}$ and 50 mM Tris-HCl buffer.

(5) Optimum temperature
Around 20° C. when allowed to react at pH7.0 for 60 minutes.

(6) Optimum pH
About pH7.0–8.0 when allowed to react at 25° C. for 60 minutes.

(7) Thermal stability
Stable up to around 30° C. when incubated at pH7.0 for 60 minutes.

(8) pH Stability
About pH6.0–9.0 when incubated at 20° C. for 60 minutes.

Maltose/trehalose conversion enzyme derived from Pseudomonas putida H262

(1) Action
Capable of converting maltose into trehalose, as as well as of converting trehalose into maltose. Forming from one mole of maltose or trehalose about one mole of trehalose or maltose respectively.

(2) Molecular weight
About 110,000–120,000 daltons on SDS-gel electrophoresis.

(3) Isoelectric point
About pI4.1–5.1 on Ampholine electrophoresis.

(4) Inhibition of activity
Inhibited by 1 mM $Cu^{2+}$, $Hg^{2+}$ and 50 mM Tris-HCl buffer.

(5) Optimum temperature
Around 37° C. when allowed to react at pH7.0 for 60 minutes.

(6) Optimum pH
About pH7.3–8.3 when allowed to react at 35° C. for 60 minutes.

(7) Thermal stability
Stable up to around 40° C. when incubated at pH7.0 for 60 minutes.

(8) pH Stability
About pH6.0–9.5 when incubated at 35° C. for 60 minutes.

Maltose/trehalose conversion enzyme derived from Thermus aquaticus ATCC33923

(1) Action
Capable of converting maltose into trehalose, as as well as of converting trehalose into maltose. Forming from one mole of maltose or trehalose about one mole of trehalose or maltose respectively.

(2) Molecular weight
About 100,000–110,000 daltons on SDS-gel electrophoresis.

(3) Isoelectric point
About pI3.8–4.8 on Ampholine electrophoresis.

(4) Inhibition of activity
Inhibited by 1 mM $Cu^{2+}$, $Hg^{2+}$ and 50 mM Tris-HCl buffer.

(5) Optimum temperature
Around 65° C. when allowed to react at pH7.0 for 60 minutes.

(6) Optimum pH
About pH6.0–6.7 when allowed to react at 60° C. for 60 minutes.

(7) Thermal stability
Stable up to around 80° C. when incubated at pH7.0 for 60 minutes.

(8) pH Stability
About pH5.5–9.5 when incubated at 60° C. for 60 minutes.

Maltose/trehalose conversion enzymes are assayed as follows: 1 ml of 20 w/v % maltose as substrate in 10 mM phosphate buffer (pH7.0) is added with 1 ml enzyme liquid, allowed to react at 25° C., 35° C. or 60° C. for 60 minutes and heated at 100° C. for 10 minutes to suspend the reaction. The reaction liquid is accurately diluted by 11-times in 50 mM phosphate buffer (pH7.5) and 0.4 ml of the diluted liquid is added with 0.1 ml of 1 unit/ml trehalase solution, incubated at 45° C. for 120 minutes and determined for glucose level by the glucose oxidase method. As control, an enzyme liquid and trehalase which have been inactivated by heating at 100° C. for 10 minutes are treated similarly as above. The amount of the trehalose formed by maltose/trehalose conversion enzyme is estimated with the increased amount of glucose as determined by the above measurement and one unit of the enzyme is defined as the amount of enzyme that forms one micromole of trehalose for one minute.

In this assay, the reaction temperature is set to 25° C. for maltose/trehalose conversion enzymes derived from the genus Pimelobacter; to 35° C. for for those derived from the genus Pseudomonas; and to 60° C. for those derived from the genus Thermus.

The starches feasible in the present invention are terrestrial starches such as corn starch, rice starch and wheat starch and subterranean starches such as potato starch, sweet potato starch and tapioca starch. To liquefy such a starch, it is usually suspended in water, desirably, to 10% or higher, more desirably, to about 20–50%, heated and subjected to mechanical, enzymatic or acid liquefaction. The liquefaction degree is relatively low, in particular, lower than 15, preferably, lower than 10 in terms of DE. In case of liquefying with acids, for example, at first, hydrochloric acid, phosphoric acid or oxalic acid is used, then calcium carbonate, calcium oxide or sodium carbonate is used for neutralization to prescribed pH. In case of liquefying with enzymes, alphaamylases, in particular, heat-resistant liquefying alphaamylases are preferred.

The beta-amylases used in the present invention to produce maltose from liquefied starch solutions can be prepared in conventional manner from plants, such as sweet potato, soy bean and wheat bran, and cultures of microorganisms of the genus Bacillus. Of course, commercially-available enzyme preparations can be arbitrarily used. While the starch-debranching enzymes feasible in the present invention are those which act on liquefied starches with relatively low DE, desirably, less than DE15, to hydrolyze the branches therein: With such purpose, conventional pullulanase and isoamylse can be favorably used, as well as commercially-available enzyme preparations.

The amounts of enzymes to be used are arbitrarily chosen dependently on reaction conditions including reaction time: Usually, against liquefied starch solutions as substrate, beta-amylase is used in an amount of about 1–100 units/g solid, while starch-debranching enzyme, about 1–2,000 units/g solid.

The maltose thus obtained can be favorably used as saccharide source for trehalose or saccharide containing the same in the cultivation according to the present invention. The timing to incorporate maltose in nutrient culture media is arbitrarily chosen and it can be incorporated before or during cultivation as far as trehalose is formed. In case of cultivating in continuous or semicontinuous manner, during cultivation, for example, a part of culture where trehalose has been formed may be taken out and a fresh nutrient culture medium with maltose of the same volume is then supplemented to the culture. Such a cultivation can be arbitrarily carried out with nutrient culture media which have been incorporated with either beta-amylase or beta-amylase and starch-debranching enzyme.

The resultant cultures with trehalose are subjected to filtration and centrifugation in conventional manner to remove insoluble substances such as cells, decolored with activated carbon, deionized, purified with ion exchanges of H- and OH-forms and concentrated into syrup products. The products can be arbitrarily dried into powder. Trehalose of the possible highest purity can be easily obtained by further purifying the syrup products with one or more methods, for example, fractionation using column chromatographies such as ion exchange column chromatography, activated carbon column chromatography and silica gel column chromatography, fractional precipitation using organic solvents such as alcohol and acetone, separation using membranes with appropriate separating abilities, fermentation treatment by yeast and alkali treatment so as to remove or to decompose the remaining reducing saccharides, if necessary.

It is favorable in industrial-scale production to use ion exchange column chromatography on strongly-acidic cation exchanges, for example, those disclosed in Japanese Patent Kokai Nos.23,799/83 and 72,598/83 so as to remove contaminant saccharides and also to increase the contents for objective trehalose. In this case, one can arbitrarily choose fixed bed method, moving bed method and simulated-moving bed method.

The saccharides containing trehalose thus obtained according to the present invention can be subjected to further processings, in particular, degradation by glucoamylase or alpha-glucosidase to control their sweetening and reducing powers and also to decrease their viscosity, or hydrogenation into alcohols so as to eliminate the reducing power due to the remaining reducing saccharides.

Especially, when the saccharide containing trehalose according to the present invention is subjected to glucoamylase or alpha-glucosidase into a mixture solution of trehalose and glucose which is then subjected to the above described purification, for example, ion exchange column chromatography for removal of glucose, one can obtain trehalose-rich fractions. The fractions can be purified and concentrated into a syrup product which may be further concentrated to a supersaturated state and crystallized into crystalline trehalose hydrate or anhydrous crystalline trehalose.

To produce crystalline trehalose hydrate, for example, a high-trehalose content liquid, purity of about 60% or higher, concentration of about 65–90%, is placed in crystallizer and gradually cooled at 95° C. or lower, desirably, at 10°–90° C., if necessary, in the presence of 0.1–20% seed crystals to obtain a massecuite which contains crystalline trehalose hydrate. In this case, one can favorably employ continuous crystallization method where trehalose is crystallized while concentrating under reduced pressure. Examples of methods which yield crystalline trehalose hydrate or saccharide mixture solid containing the same from such a massecuite include conventional crystal separation method, block pulverization method, fluidized-bed granulation method and spray drying method.

Crystal separation method is suitable to produce crystalline trehalose hydrate with an elevated purity, where massecuites are usually fed to basket-type centrifuge where they are separated into crystalline trehalose hydrate and mother liquor, after which the former crystals are sprayed with a minimum amount of chilled water for washing. In spray drying method, massecuites, concentration of 70–85%, crystallizing ratio up to 20–60%, are usually sprayed through a nozzle combined with a high pressure pump, dried within a stream of hot air at a temperature where crystalline powder does not melt, for example, 60°–100° C. and aged in a stream of hot air, temperature of 30°–60° C., for about 1–20 hours, thus easily obtaining non- or less-hygroscopic crystalline mixture solids. In the block pulverization method, massecuites with moisture contents of 10–20%, crystallizing ratio up to 10–60%, are usually crystallized by allowing to stand for about 0.1–3 days into solids in block form which are then pulverized and dried by cutting or scraping, thus obtaining non- or less-hygroscopic crystalline mixture solids.

While to produce anhydrous crystalline trehalose, crystalline trehalose hydrate is converted by drying and, alternatively, a concentrated high-trehalose content liquid, moisture content less than 10%, is usually placed in crystallizer and stirred at 50°–160° C., desirably, 80°–140° C., in the presence of seed crystals to obtain a massecuite which is then crystallized and pulverized, for example, by block pulverization method, fluidized-bed granulation method and spray drying method under relatively hot and dried conditions.

The trehalose or saccharide containing the same both according to the present invention thus obtained neither cause browning and unpleasant smell nor damage in other substances, in particular, those with amino acids, such as amino acids, oligopeptides and proteins when mixed or processed therewith because the saccharides are stable due to their decreased reducing powers. Further they are low in reducing power and viscosity commonly exhibiting a high-quality and mild sweetness.

Further the trehalose according to the present invention is digested, absorbed and utilized as calorie when orally intaken because it is degraded by trehalase. Still further it is feasible as less dental caries-causative sweetener because they are hardly fermented by dental caries-causative microorganisms. Still further it bears other desirable properties such as osmosis controlling ability, shape imparting ability, gloss imparting ability, moisture retaining ability, viscosity, ability of preventing crystallization of other saccharides, decreased fermentability and ability of preventing retrogradation of gelatinized starch.

The trehalose according to the present invention can be favorably used for energy supplement to living bodies because it is readily metabolized and utilized with no fears of toxicity and side effect when parenterally used in intubation feeding or infusion form. Crystalline trehalose hydrate can be favorably used as coating agent for tablets in combination with binders such as pullulan, hydroxyethyl starch and polyvinyl pyrrolidone because trehalose acts as stable sweetener.

While anhydrous crystalline trehalose can be favorably used as desiccant for hydrous substances such as food products, cosmetics, medicines and materials and intermediates thereof to facilitate the production of stable and high-quality solid products including powders, granules and tablets.

Thus the trehalose or saccharide containing the same both according to the present invention can be favorably used as sweetener, taste improving agent, quality improving agent, stabilizer, shape imparting agent and desiccant in a variety of compositions including food products, tobacco, cigarette, feeds, cosmetics and medicines.

The trehalose or saccharide containing the same both according to the present invention can be used intact as seasoning for sweetening. If necessary, they can be mixed with an appropriate amount of one or more other sweeteners and/or fillers, for example, starch syrup powder, glucose, maltose, sucrose, isomerized sugar, honey, maple sugar, isomaltooligosaccharide, galactooligosaccharide, fructooligosaccharide, lactosucrose, sorbitol, maltitol, lactitol, dihydrochalcone, stevioside, alpha-glycosyl stevioside, rhebaudioside, glycyrrhizin, L-aspartyl-L-phenylalanine methyl ester, saccharin, glycine, alanine, dextrin, starch and lactose, prior to use.

The trehalose or saccharide containing the same in powder or crystalline form both according the present invention can be shaped intact or, if necessary, along with filler, vehicle and binder into desired shapes, for example, granule, globe, rod, plate, cube and tablet.

The trehalose or saccharide containing the same both according to the present invention can be favorably used to sweeten and/or to improve the tastes and qualities in food products in general because they are superiorly harmonize with a variety of substances with other types of tastes such as sour, salty, astringent, delicious and bitter tastes.

For example, they can be favorably used, for example, in a variety of seasonings such as amino acids, peptides, soy sauce, powdered soy sauce, miso, powdered miso, "moromi", "hishio", "furikake", mayonnaise, dressing, vinegar, "sanbaizu", powdered vinegar for "sushi", "chuka-no-moto", "tentsuyu", "mentsuyu", sauce, catsup, "yakiniku-no-tare", curry roux, stew stock, soup stock, "dashi-no-moto", nucleic acid seasoning, mixed seasoning, "mirin", "shin-mirin", table sugar and coffee sugar.

Further they can be favorably used to sweeten and/or to improve the tastes and qualities, for example, in a variety of Japanese-style confectioneries such as "senbei", "arare", "okoshi", "ame", "manju", "uiro", bean pastes, "yokan", "mizuyokan", "kingyoku", jelly, castella and "amedama"; Western-style confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as preserved fruits and "kori-mitsu"; pastes such as flour paste, peanut paste, fruit paste and spread; processed fruits and vegetables such as jam, marmalade, preserved fruits and vegetables and "toka"; pickles and pickled products such as "fukuzin-zuke", "bettara-zuke", "senmai-zuke" and "rakkyo-zuke"; stocks for pickled products such as "takuan-zuke-no-moto" and "hakusai-zuke-no-moto"; meat products such as ham and sausage; fish meat products such as fish meat ham, fish meat sausage, "kamaboko", "chikuwa" and "tenpura"; relish such as "uni-no-shiokara", "ika-no-shiokara", "su-konbu", "saki-surume" and "fugu-no-mirin-boshi"; "tsukudani" such as those of seaweed, "sansai", "surume", small fish and shellfish; daily dishes such as "nimame", potato salad and "konbu-maki"; milk product such as yoghurt and cheese; canned and bottled products such as those of fish meat, meat, fruits and vegetables; alcohol drinks such as sake, synthetic sake, liquors and Western-style alcoholic drinks; soft drinks such as coffee, tea, cocoa, juice, carbonated drink, lactic acid drink and drink containing lactic acid bacteria; convenient foods such as pudding mix, hot cake mix, "sokuseki-shiruko" and convenient soup; and other types of food products such as infants' foods, treatment foods, bottled beverages, peptide foods, chilled foods and dried foods.

Still further they can be favorably used with the purpose to improve taste qualities of feeds such as those for domestic animals, poultries, honey bees, silk worm and fish. They are also favorably used in a variety of compositions in solid, paste or liquid form such as tobacco, cigarette, cosmetics and medicines including dentifrice, lip stick, lip cream, internal medicine, tablet, troche, cod liver oil drop, oral refreshing agent and gargle.

The uses as quality improving or stabilizer include those for a variety of bioactive substances and health foods and medicines containing the same whose effective ingredients and activities are susceptible to inactivation. Example of such a bioactive substance are lymphokines such as interferonalpha, interferon-beta, interferon-gamma, tumor necrosis factor-alpha, tumor necrosis factor-beta, macrophage migration inhibitory factor, colony stimulating factor, transfer factor and interleukin 2; hormones such as insulin, growth hormone, prolactine, erythropoietin and follicle stimulating hormone; biological preparations such as BCG vaccine, Japanese encephalitis virus vaccine, measles vaccine, poliomyelitis vaccine, smallpox vaccine, tetanus toxoid, Trimeresurus antitoxin and human immunoglobulin; antibiotics such as penicillin, erythromycin, chroramphenicol, tetracycline, streptomycin and kanamycin sulfate; vitamins such as thiamin, riboflavin, L-ascorbic acid, cod liver oil, carotenoid, ergosterol and tocopherol; enzymes such as lipase, elastase, urokinase, protease, beta-amylase, isoamylase, glucanase and lactase; extracts such as those of ginseng, snapping turtle, chlorella, aroe and pro-polis; live microorganisms such as live virus, lactic acid bacteria and yeast; and other type of bioactive substances including royal jelly. Thus one can easily produce stable and high-quality health foods and medicines in liquid, paste or solid form without loosing their activities or effective ingredients.

To incorporate in such a composition the trehalose or saccharide containing the same, they are incorporated by conventional methods, for example, mixing, dissolving, melting, soaking, permeating, spreading, applying, coating, spraying, injecting, crystallizing and solidifying prior to completion of their processings. The amounts to be incorporated are usually 0.1% or more, desirably, 1% or more. The present invention will be more concretely explained with reference to several Experiments.

At first maltose/trehalose conversion enzymes from novel microorganisms Pimelobacter species R48 and *Pseudomonas putida* H262 and *Thermus aquaticus* (ATCC33923), then those from conventional microorganisms will be explained.

Experiment 1
Production of enzyme

One hundred ml aliquots of a liquid culture medium consisting of 2.0 w/v % glucose, 0.5 w/v % polypepton, 0.1 w/v % yeast extract, 0.1 w/v % dipotassium hydrogen phosphate, 0.06 w/v % sodium dihydrogen phosphate, 0.05 w/v % magnesium sulfate heptahydrate, 0.5 w/v % calcium carbonate and water were distributed in 500 ml flasks, autoclaved at 115° C. for 30 minutes for sterilization, cooled, inoculated with a stock culture of Pimelobacter species R48 (FERM BP-4315) and cultivated at 27° C. and 200 rpm for 24 hours under shaking conditions to obtain a seed culture.

About 20 liters of a fresh preparation of the same culture medium as described above was placed in 30 liter fermenter, sterilized by heating, cooled to 27° C., inoculated with 1 v/v % seed culture and cultivated for about 40 hours under aeration and agitation conditions while retaining at 27° C. and pH6.0–8.0.

The activity of maltose/trehalose conversion enzyme in the culture was about 0.55 units/ml. A portion of the culture was sampled and centrifugally separated into cells and supernatant and the cells were then suspended in 50 mM phosphate buffer (pH7.0) to give the same volume as that of the sampled culture, followed by determining the enzymatic activities in the cell suspension and supernatant, revealing that about 0.5 units/ml of enzymatic activity was found in the cell suspension, while about 0.05 units/ml, in the supernatant. The enzymatic activities were determined at 25° C.

Experiment 2
Purification of enzyme

The culture obtained in Experiment 1 was centrifugally separated to collect the cells, about 0.5 kg wet weight, which were then suspended in 10 mM phosphate buffer (pH7.0). The cell suspension, about 5 liters, was subjected to "VIBROGEN ZELLMUHLE", a cell disrupter commercialized by Edmund Buhler, to disrupt the cells and the resultant was centrifuged at 15,000 rpm for 30 minutes to obtain about 4.5 liters of a supernatant. The supernatant was added with ammonium sulfate to give a saturation degree of 0.3, allowed to stand at 4° C. for 4 hour and centrifuged, followed by recovering the supernatant.

The supernatant was further added with ammonium sulfate to give a saturation degree of 0.8, allowed to standing at 4° C. overnight and centrifuged to recover the sediment.

The sediment was dissolved in 10 mM phosphate buffer (pH7.0), dialyzed against a fresh preparation of the same buffer for 24 hours and centrifuged to remove insoluble substances. The dialyzed solution, about 400 ml, was divided into two portions which were then separately applied to ion exchange column chromatography on 300 ml "DEAE TOYOPEARL".

The maltose/trehalose conversion enzyme according to the present invention, which had been adsorbed on "DEAE TOYOPEARL", was eluted therefrom with a fresh preparation of the same buffer but additionally containing sodium chloride. The enzymatically active fractions thus obtained were dialyzed against a fresh preparation of the same buffer but additionally containing 1M ammonium sulfate and centrifuged to remove insoluble substances, after which the obtained supernatant was subjected to a hydrophobic column chromatography on 300 ml "BUTYL TOYOPEARL 650". The maltose/trehalose conversion enzyme which had been adsorbed in the column was eluted therefrom under a linear gradient decreasing from 1M to 0M for ammonium sulfate, followed by recoverying the enzymatically active fractions.

The fractions were then applied to ion exchange chromatography on 10 ml "MONO Q HR5/5" commercialized by Pharmacia LKB, Uppsala, Sweden, and the enzymatically active fractions were recovered. The enzymatic activities, specific activities and yields in respective purification stages were as shown in Table 1.

TABLE 1

| Purification stage | Enzymatic activity (units) | Specific activity (units/mg protein) | Yield (%) |
| --- | --- | --- | --- |
| Supernatant of disrupted culture | 7,310 | 0.13 | 100 |
| Liquid after salting out by ammonium sulfate and dialysis | 2,730 | 0.16 | 37.3 |
| Eluate of ion exchange column chromatography | 2,290 | 0.68 | 31.3 |
| Eluate of hydrophobic column chromatography | 1,160 | 5.4 | 15.9 |
| Eluate of ion exchange column chromatography | 819 | 16.8 | 11.2 |

After checking the purity of the purified enzyme on polyacrylamide gel electrophoresis, gel concentration of 7.5 w/v %, it gave a single band of protein confirming that it was homogenous and highly pure.

Experiment 3
Properties of enzyme

A purified maltose/trehalose conversion enzyme obtained by the method in Experiment 2 was subjected to SDS-polyacrylamide gel electrophoresis, gel concentration of 10 w/v %, and determined for molecular weight by comparing with those of the molecular weight markers commercialized by Japan Bio-Rad Laboratories, Tokyo, Japan, which had been electrophoresed on the same gel, revealing that the molecular weight of the enzyme was about 57,000–67,000 daltons.

The purified maltose/trehalose conversion enzyme was electrophoresed on polyacrylamide gel using 2 w/v % Ampholine commercialized by Pharmacia LKB, Uppsala, Sweden, and the pH levels of the protein bands and gel were determined, revealing that the isoelectric point of the enzyme was about pI4.1–5.1.

Figure 2:
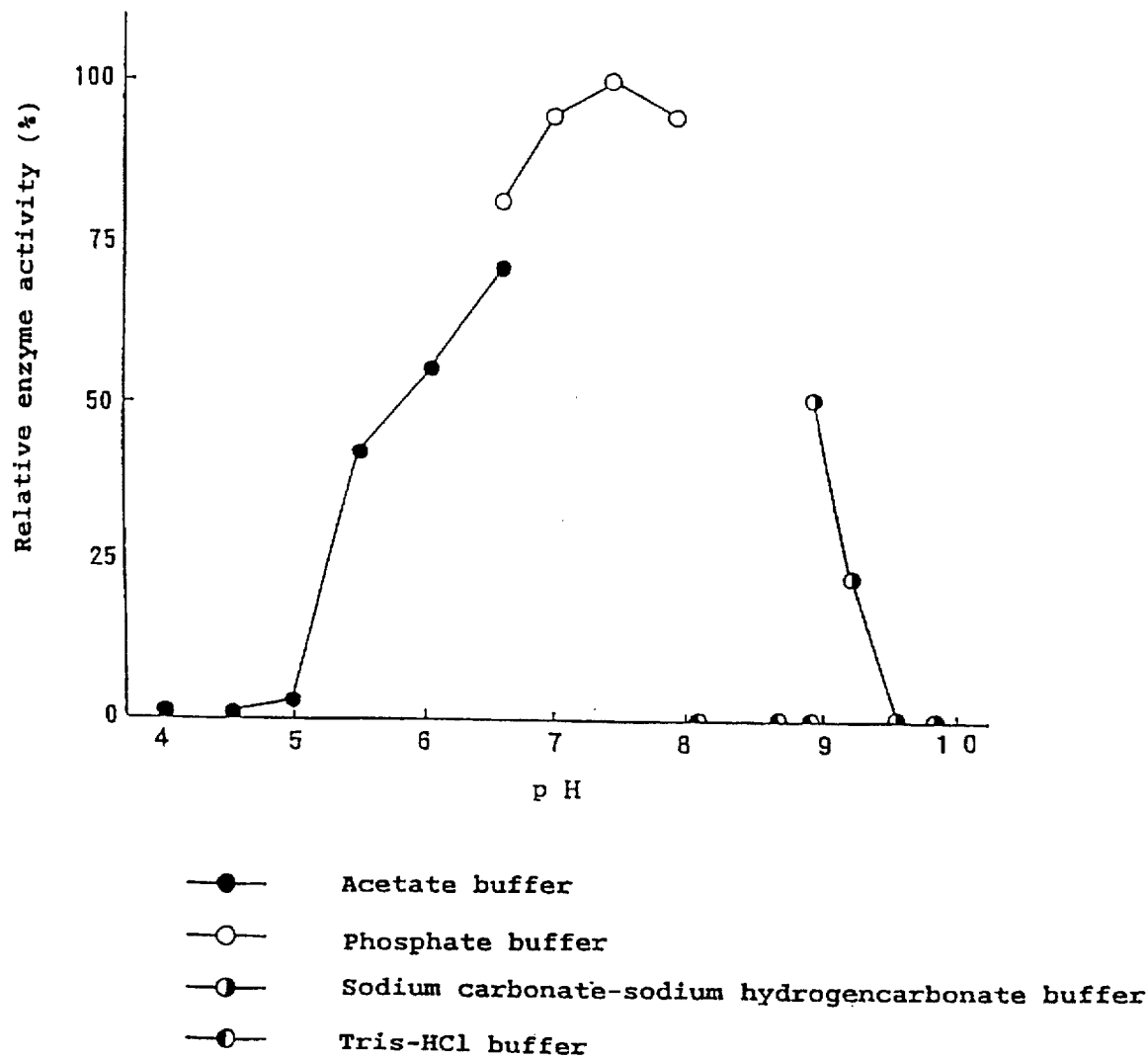
FIG. 2 shows the effect of pH on the activity of the maltose/trehalose conversion enzyme derived from Pimelobacter species R48.
Figure 3:
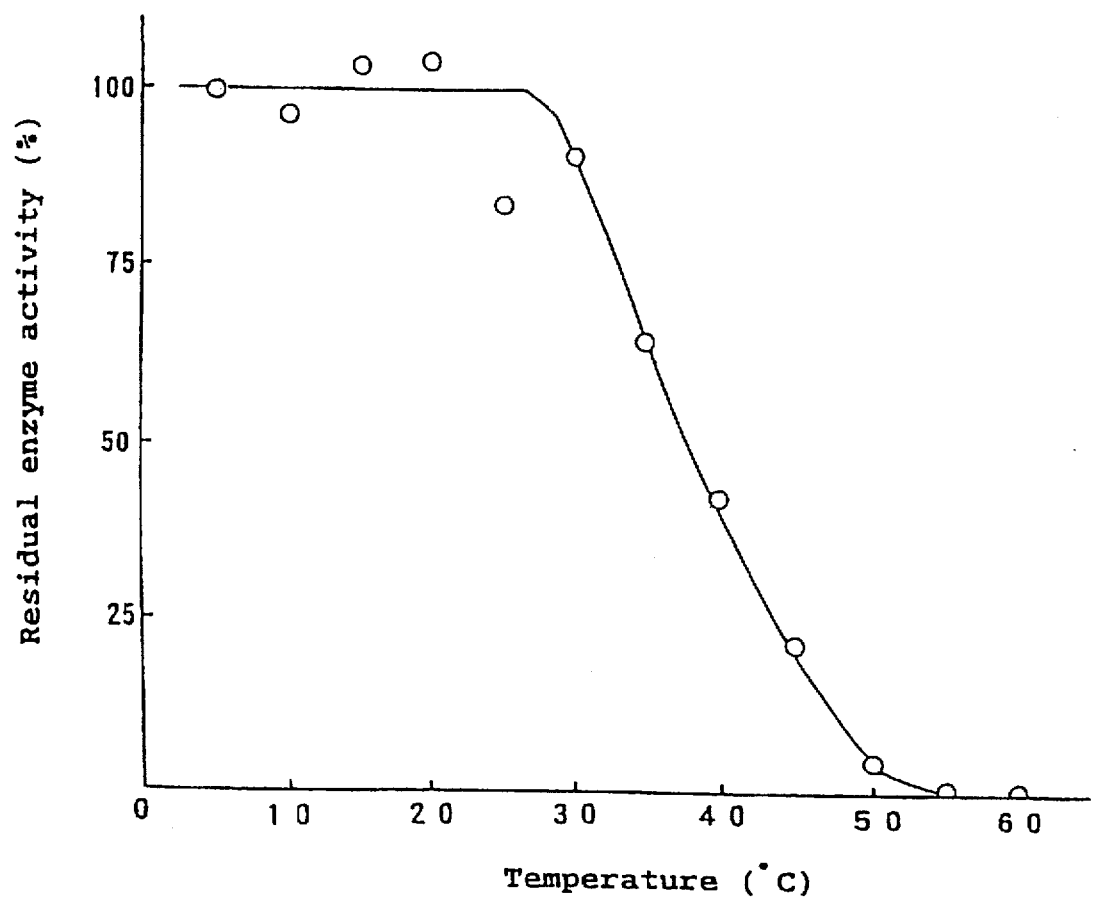
FIG. 3 shows the thermal stability of the maltose/trehalose conversion enzyme derived from Pimelobacter species R48.
Figure 4:
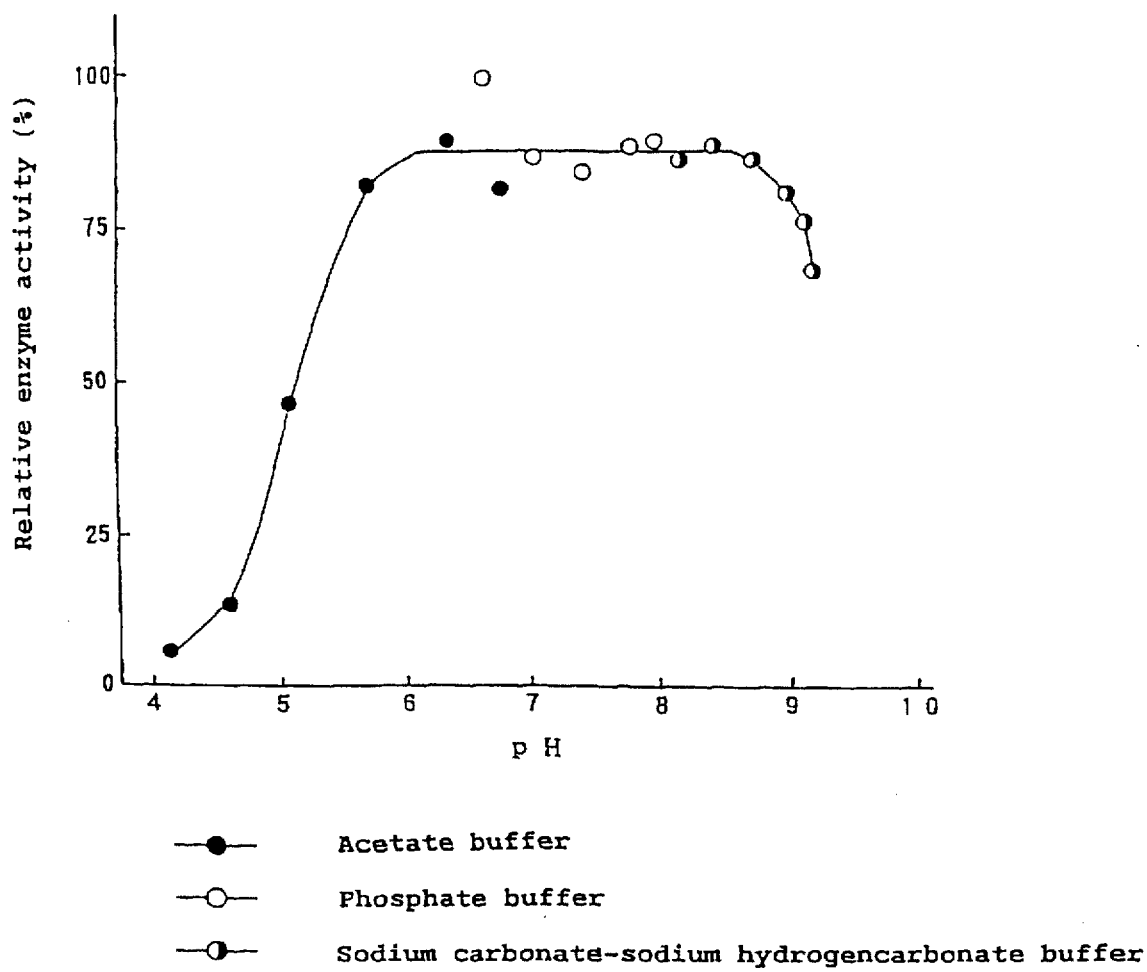
FIG. 4 shows the pH stability of the maltose/trehalose conversion enzyme derived from Pimelobacter species R48.

Effects of temperature and pH on the activity of the enzyme were investigated in accordance with the assay method. The results were as shown in FIG. 1 for the effect of temperature and in FIG. 2 for the effect of pH. The optimum temperature of the enzyme was around 20° C. when allowed to react at pH7.0 for 60 minutes, while the optimum pH, about 7.0–8.0 when allowed to react at 25° C. for 60 minutes. The thermal stability of the enzyme was determined by incubating the enzyme in 50 mM phosphate buffer (pH7.0) at different temperatures for 60 minutes, cooling with water and assaying the residual activities. While the pH stability was determined by incubating at 20° C. for 60 minutes in 50 mM phosphate buffer with different pH levels, adjusting to pH7.0 and assaying the residual enzyme activities. Respective results were as shown in FIG. 3 for the thermal stability and in FIG. 4 for the pH stability. The thermal stability was up to about 30° C., while the pH stability, about pH6.0–9.0. The enzymatic activity was inhibited by 1 mM $Cu^{2+}$, $Hg^{2+}$ and 50 mM Tris-HCl buffer.

Experiment 4

Action on a variety of saccharides

A variety of saccharides were tested for feasibility as substrate. Provided were solutions of either glucose, maltose, maltotriose, maltotetraose, maltopentaose, maltohexaose, maltoheptaose, soluble starch, amylase with an averaged polymerization degree of 18, trehalose, neotrehalose, gentiobiose, kojibiose, isomaltose, cellobiose, maltitol, sucrose, maltulose, turanose, palatinose, trehalulose or lactose and solutions which contained glucose together with the same amount of either alpha-glucose 1-phosphate or beta-glucose 1-phosphate.

Each solution was added with 2 units/g substrate solid of a purified maltose/trehalose conversion enzyme obtained by the method in Experiment 2, adjusted to give respective substrate concentrations of 5 w/v % and reacted at 20° C. and pH7.0 for 24 hours. Before and after the reaction the solutions were subjected to thin-layer chromatography (TLC) on "KIESELGEL 60", an aluminum plate, width and length of 20 cm respectively, commercialized by Merck & Co., Inc., New Jersey, U.S.A., to check the enzymatic action on respective saccharides. TLC was developed at ambient temperature with a mixture solvent of 1-butanol, pyridine and water (6:4:1 by volume). Coloration was carried out by first spraying 20% sulfuric acid/methanol solution, then heating at 110° C. for 10 minutes. The results were as shown in Table 2.

TABLE 2

| Substrate | Enzymatic action |
|---|---|
| Glucose | – |
| Maltose | ++ |
| Maltotriose | – |
| Maltotetraose | – |
| Maltopentaose | – |
| Maltohexaose | – |
| Maltoheptaose | – |
| Soluble starch | – |
| Amylose with an averaged polymerization degree of 18 | – |
| Trehalose | + |

TABLE 2-continued

| Substrate | Enzymatic action |
|---|---|
| Neotrehalose | – |
| Gentiobiose | – |
| Kojibiose | – |
| Isomaltose | – |
| Cellobiose | – |
| Maltitol | – |
| Sucrose | – |
| Maltulose | – |
| Turanose | – |
| Palatinose | – |
| Trehalulose | – |
| Lactose | – |
| Alpha-glucose 1-phosphate + glucose | – |
| Beta-glucose 1-phosphate + glucose | – |

Note: The symbol "–" means that no changes were observed before and after the reaction; "+", spots of substrates were significantly decreased and reaction products were detected; and "++", spots of substrates substantially decreased and reaction products were detected.

As evident from the results in Table 2, among a variety of saccharides as tested, the enzyme according to the resent invention acted on only maltose and trehalose but did not act on other saccharides, in particular, on the systems which contained glucose and either alpha-glucose 1-phosphate or beta-glucose 1-phosphate, confirming that the enzyme was novel and different from conventional maltose phosphorylase and trehalose phosphorylase.

Experiment 5

Products from maltose or trehalose

An aqueous maltose solution, final concentration of 5%, was added with 2 units/g substrate solid of a purified maltose/trehalose conversion enzyme obtained by the method in Experiment 2 and reacted at 20° C. and pH7.0 for 24 hours. The saccharide composition of the enzymatic reaction liquid was analyzed on gas chromatography (GLC). A portion of the enzymatic reaction liquid was solidified by drying, dissolved in pyridine and trimethylsililated prior to analysis. The GLC apparatus used was "GC 16A", commercialized by Shimazdu Corp., Kyoto, Japan, equipped with a stainless steel column, inner diameter of 3 mm, length of 2 m, packed with "2% SILICONE OV-17/CHROMOSORB W" commercialized by GL Sciences, Tokyo, Japan, which was injected with nitrogen gas as carrier at a flow rate of 40 ml/minute while elevating the temperature inside the column from 160° C. to 320° C. at a rate of 7.5° C./minute. The detector used was a hydrogen flame ionization detector. The results were as shown in Table 3.

TABLE 3

| Saccharide in reaction product | Retention time on GLC (minute) | Saccharide composition (%) |
|---|---|---|
| Glucose | 3.87 and 4.70 | 4.9 |
| Maltose | 11.9 and 12.27 | 22.3 |
| Reaction product X | 12.34* | 72.8 |

Note: The symbol "*" means that the retention time was the same as that of trehalose.

As evident from the results in Table 3, it was found that a large amount of reaction product "X" was formed, which marked the same retention time as that of commercially-available trehalose. To identify the reaction product "X", the following confirmation tests were carried out. A portion of the enzymatic reaction product from maltose as substrate was diluted to give a saccharide concentration of 2% in 20 mM acetate buffer (pH4.5) and 0.5 ml of the resultant was sampled, added with 0.1 unit of glucoamylase commercialized by Seikagaku Corp., Tokyo, Japan, and reacted at 40° C. for 20 hours.

Another portion of the enzymatic reaction product was diluted to give a saccharide concentration of 2% in 20 mM phosphate buffer (pH7.0) and 0.5 ml of the resultant was added with 0.5 units of tehalase and reacted at 40° C. for 20 hours. The enzymatic reaction product from maltose as substrate and its glucoamylase- or trehalase-treated products were analyzed on GLC and compared each other, confirming that maltose was completely degraded into glucose by glucoamylase, while the reaction product "X" was not degraded and left intact.

Further after trehalase treatment maltose was left intact, while the reaction product "X" was completely degraded into glucose. Considering the reaction specificities of glucoamylase and trehalase, the oligosaccharide which was formed from maltose by the novel enzyme according to the present invention was identified trehalose.

Still further trehalose as substrate was subjected to the purified enzyme under the same conditions as in the case of maltose and the reaction liquid was analyzed similarly on GLC, confirming that the enzyme according to the present invention formed maltose from trehalose. The results of the above GLC analysis were as shown in Table 4.

As evident from the results in Table 4, the enzyme according to the present invention converts maltose into trehalose, as well as converting trehalose into maltose. It was found that the equilibrium point was declined to the trehalose side and therefore the conversion ratio from maltose into trehalose was high, in particular, about 70% or higher.

TABLE 4

| Substrate | Saccharides in reaction products | A | B | C |
|---|---|---|---|---|
| Maltose | Glucose | 4.9 | 27.9 | 78.5 |
|  | Maltose | 22.3 | 0.0 | 21.5 |
|  | Trehalose | 72.8 | 72.1 | 0.0 |
| Trehalose | Glucose | 3.2 | 19.9 | 83.3 |
|  | Maltose | 17.2 | 0.0 | 16.7 |
|  | Trehalose | 79.6 | 80.1 | 0.0 |

Note: The symbol "A" means the saccharide compositions (%) in reaction products by the enzyme according to the present invention; "B", the saccharide compositions (%) after glucoamylase treatment; and "C", the saccharide compositions (%) after trehalase treatment.

Experiment 6
Effect of maltose concentration on the formation of trehalose

Maltose solutions, concentration of either 2.5%, 5%, 10%, 20% or 40%, were added with 2 units/g maltose solid of a purified maltose/trehalose conversion enzyme obtained by the method in Experiment 2 and reacted at 20° C. and pH7.0 and during the reaction the reaction liquids were periodically sampled and heated at 100° C. for 10 minutes to inactivate the enzyme.

The reaction liquids were quantitatively determined for total sugar by the anthrone-sulfuric acid method and for reducing sugar by the Somogyi-Nelson method and the ratios of reducing saccharide against total saccharide as the reducing power were calculated.

Separately the reaction liquids were diluted to give respective saccharide concentrations of about 1%, subjected to "MOLCUT II LGC", a miniaturized ultrafilter commercialized by Japan Millipore Ltd., Tokyo, Japan, for removal of proteins and then analyzed on high-performance liquid chromatography (HPLC) for saccharide composition. The HPLC apparatus as used was "CCPD SYSTEM" commercialized by Tosoh Corp., Tokyo, Japan, equipped with "YMC-PACK PA-03", inner diameter of 4.6 mm, length of 250 mm, an analytical column commercialized by YMC Co., Ltd., Kyoto, Japan, which was injected as eluent a mixture of acetonitrile and water (78:22 by volume) at a flow rate of 1.2 ml/minute, and the detection was carried out with differential reflactometer. The results were as shown in Table 5.

As evident from the results in Table 5, the conversion from maltose into trehalose readily proceeded independently on the concentration of maltose as substrate marking a conversion rate of about 80%.

TABLE 5

| Maltose | Reaction | Reducing | Saccharide composition (%) | | |
|---|---|---|---|---|---|
| (%) | time (hour) | power (%) | Glucose | Maltose | Trehalose |
|  | 0 | 50.3 | 0.0 | 100.0 | 0.0 |
| 2.5 | 2 | 36.7 | 1.3 | 68.8 | 29.9 |
|  | 8 | 21.2 | 2.5 | 38.7 | 58.8 |
|  | 23 | 12.3 | 3.8 | 17.2 | 79.0 |
|  | 48 | 14.5 | 5.9 | 17.1 | 79.5 |
| 5.0 | 2 | 34.8 | 1.9 | 65.3 | 32.8 |
|  | 8 | 20.2 | 2.6 | 35.7 | 61.7 |
|  | 23 | 12.0 | 3.2 | 17.3 | 77.0 |
|  | 48 | 14.2 | 5.7 | 17.3 | 77.0 |
| 10.0 | 2 | 32.2 | 1.3 | 63.0 | 35.7 |
|  | 8 | 19.7 | 2.2 | 34.2 | 63.6 |
|  | 23 | 12.5 | 3.6 | 17.5 | 78.9 |
|  | 48 | 14.0 | 6.1 | 17.4 | 76.5 |
| 20.0 | 2 | 34.2 | 2.0 | 63.7 | 34.3 |
|  | 8 | 20.2 | 2.9 | 35.1 | 62.0 |
|  | 23 | 12.9 | 3.4 | 17.4 | 79.2 |
|  | 48 | 15.1 | 6.0 | 17.4 | 76.6 |
| 40.0 | 2 | 34.8 | 1.6 | 68.2 | 30.2 |
|  | 8 | 21.2 | 2.7 | 38.6 | 58.7 |
|  | 23 | 12.8 | 3.7 | 17.7 | 78.6 |
|  | 48 | 14.9 | 5.7 | 17.5 | 76.8 |

Experiment 7
Effect of temperature of the formation of trehalose

Maltose solutions, concentration of 20% each, were adjusted to pH7.0, added with 2 units/g maltose solid of a purified maltose/trehalose conversion enzyme obtained by the method in Experiment 2 and reacted at either 5° C., 10° C., 15° C., 20° C. or 25° C. and during the reaction the reaction liquids were periodically sampled and heated at 100° C. for 10 minutes to inactivate the enzyme. The enzymatic reaction liquids were analyzed on HLPC for saccharide composition similarly as in Experiment 6. The trehalose contents at respective reaction temperatures and times were as shown in Table 6.

TABLE 6

| Reaction time | Trehalose content (%) | | | | |
|---|---|---|---|---|---|
| (hour) | 5° C. | 10° C. | 15° C. | 20° C. | 25° C. |
| 2 | 26.1 | 28.9 | 32.9 | 34.6 | 34.7 |
| 8 | 49.5 | 54.3 | 61.2 | 62.0 | 61.1 |
| 23 | 78.2 | 79.5 | 80.9 | 79.2 | 76.7 |
| 48 | 81.8 | 80.9 | 80.4 | 76.6 | 72.7 |

As evident from the results in Table 6, although the formation rate for trehalose was more readily at a higher temperature, even at 5° C., the conversion from maltose into trehalose readily proceeded marking a conversion rate of about 82%.

Experiment 8
Preparation of trehalose from maltose

Ten parts by weight of maltose commercialized by Hayashibara Biochemical Laboratories, Inc., Okayama, Japan, was dissolved in 40 parts by weight of water, added at 15° C. and pH7.0 to 2 units/g maltose solid of a purified maltose/trehalose conversion enzyme obtained by the method in Experiment 2, reacted for 48 hours and heated at 100° C. for 10 minutes to inactivate the enzyme. The resultant solution contained about 74% trehalose on dry solid basis. The solution was then decolored with activated carbon, deionized and purified with ion exchanges of H- and OH-forms, concentrated to about 78%, added with 0.1% crystalline trehalose hydrate as seed crystal on dry solid basis and allowed to standing at ambient temperature overnight to effect crystallization. The resultant massecuite was separated and the crystals were sprayed with a minimum amount of water for washing, thus obtaining about 3.0 parts by weight of an extremely pure crystalline trehalose hydrate, purity of 99.8%.

Experiment 9
Production of enzyme

One hundred ml aliquots of a liquid culture medium consisting of 2.0 w/v % glucose, 1.0 w/v % ammonium sulfate, 0.1 w/v % dipotassium hydrogen phosphate, 0.06 w/v % sodium dihydrogen phosphate, 0.05 w/v % magnesium sulfate, 0.3 w/v % calcium sulfate and water were distributed in 500 ml flasks, autoclaved at 115° C. for 30 minutes for sterilization, cooled, inoculated with a stock culture of *Pseudomonas putida* (FERM BP-4579) and cultivated at 27° C. and 200 rpm for 24 hours under shaking conditions to obtain a seed culture.

About 20 liters of a fresh preparation of the same liquid culture medium as above was placed in 30 liter fermenter, sterilized by heating, cooled to 27° C., inoculated with 1 v/v % seed culture and cultivated at 27° C. for 20 hours under aeration and agitation conditions while retaining at 27° C. and pH6.5–8.0.

The activity of maltose/trehalose conversion enzyme in the culture was about 0.12 units/ml. A portion of the culture was sampled and centrifugally separated into cells and supernatant and the cells were then suspended in 50 mM phosphate buffer (pH7.0) to give the same volume as that of the sampled culture, followed by determining the enzymatic activities in the cell suspension and supernatant, revealing that about 0.11 units/ml of enzyme activity was found in the cell suspension, while about 0.01 units/ml, in the supernatant. The enzymatic activities were determined at 35° C.

Experiment 10
Purification of enzyme

The culture obtained in Experiment 9 was centrifugally separated to collect the cells, about 0.45 kg wet weight, which were then suspended in 10 mM phosphate buffer (pH7.0). The cell suspension was subjected to "MINI LABO", a super high-pressure cell disrupter commercialized by Dainippon Pharmaceutical Co., Ltd., Tokyo, Japan, to disrupt the cells and the resultant was centrifuged at 15,000 rpm for 30 minutes to obtain about 1.7 liters of a supernatant. The supernatant was added with ammonium sulfate to give a saturation degree of 0.7, allowed to standing at 4° C. overnight and centrifuged, followed by recovering the sediment.

The sediment was dissolved in 10 mM phosphate buffer (pH7.0), dialyzed against a fresh preparation of the same buffer for 24 hours and centrifuged to remove insoluble substances. The dialyzed solution, about 400 ml, was divided into two portions which were then separately applied to ion exchange column chromatography on 300 ml "DEAE TOYOPEARL".

The maltose/trehalose conversion enzyme according to the present invention, which had been adsorbed on "DEAE TOYOPEARL", was eluted therefrom with a fresh preparation of the same buffer but additionally containing sodium chloride. The enzymatically active fractions were further subjected to ion exchange column chromatography on 80 ml "DEAE TOYOPEARL". The maltose/trehalose conversion enzyme which had been adsorbed in the column was eluted therefrom under a linear gradient increasing from 0.1M to 0.3M for sodium chloride, followed by recoverying the enzymatically active fractions.

The fractions were applied to gel filtration chromatography on 400 ml "TOYOPEARL HW-55S" commercialized by Tosoh Corp., Tokyo, Japan, and the enzymatically active fractions were recovered. The enzymatic activities, specific activities and yields in respective purification stages were as shown in Table 7.

TABLE 7

| Purification stage | Enzymatic activity (units) | Specific activity (units/mg protein) | Yield (%) |
| --- | --- | --- | --- |
| Supernatant of disrupted culture | 1,750 | 0.04 | 100 |
| Liquid after salting out by ammonium sulfate and dialysis | 1,200 | 0.07 | 68.5 |
| Eluate of the first ion exchange column chromatography | 1,090 | 0.53 | 62.3 |
| Eluate of the second ion exchange column chromatography | 360 | 4.5 | 20.6 |
| Eluate of gel filtration column chromatography | 156 | 6.5 | 8.9 |

After checking the purity of the purified enzyme on polyacrylamide gel electrophoresis, gel concentration of 7.5 w/v %, it gave a single band of protein confirming that it was homogenous and highly pure.

Experiment 11
Properties of enzyme

A purified maltose/trehalose conversion enzyme obtained by the method in Experiment 10 was subjected to SDS-polyacrylamide gel electrophoresis, gel concentration of 7.5 w/v %, and determined for molecular weight by comparing with those of the molecular weight markers commercialized by Japan Bio-Rad Laboratories, Tokyo, Japan, which had been electrophoresed on the same gel, revealing that the molecular weight of the enzyme was about 110,000–120,000 daltons.

The purified maltose/trehalose conversion enzyme was electrophoresed on polyacrylamide gel using 2 w/v % Ampholine commercialized by Pharmacia LKB, Uppsala, Sweden, and the pH levels of the protein bands and gel were determined, revealing that the isoelectric point of the enzyme was about pI4.1–5.1.

Figure 5:
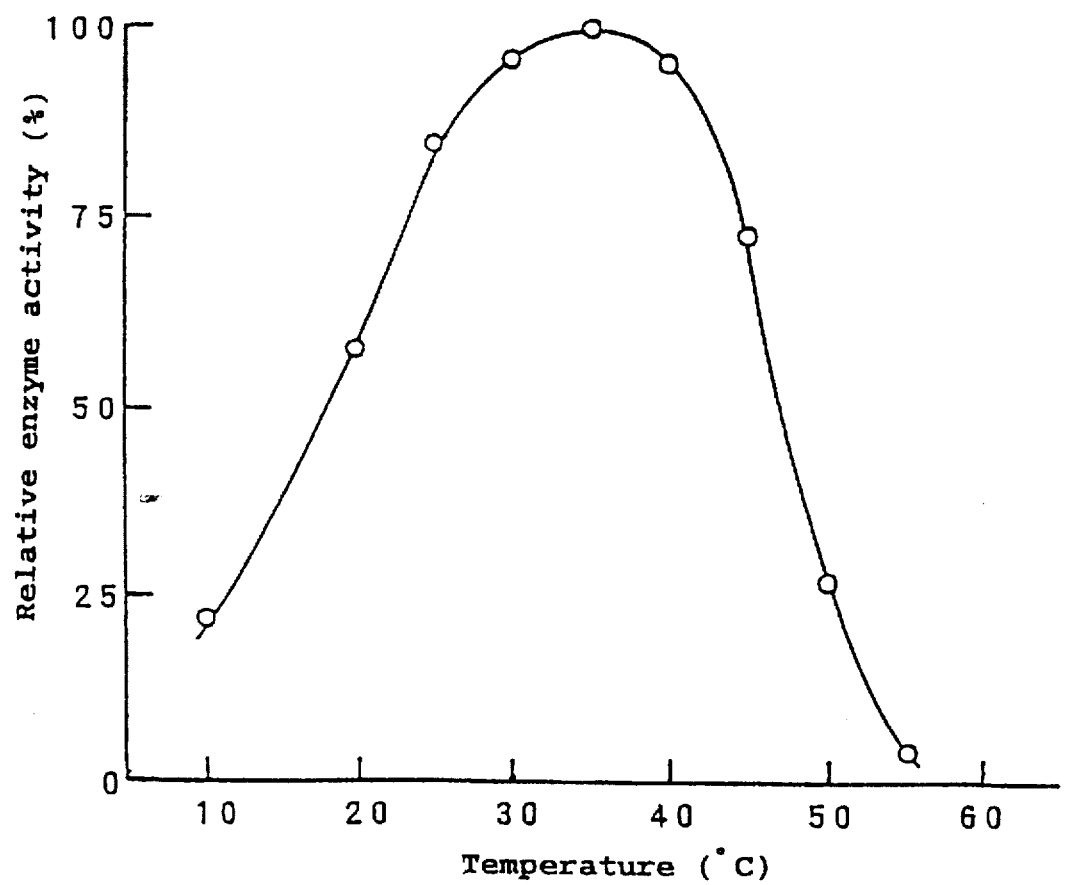
FIG. 5 shows the effect of temperature on the activity of the maltose/trehalose conversion enzyme derived from *Pseudomonas Putida* H262.
Figure 6:
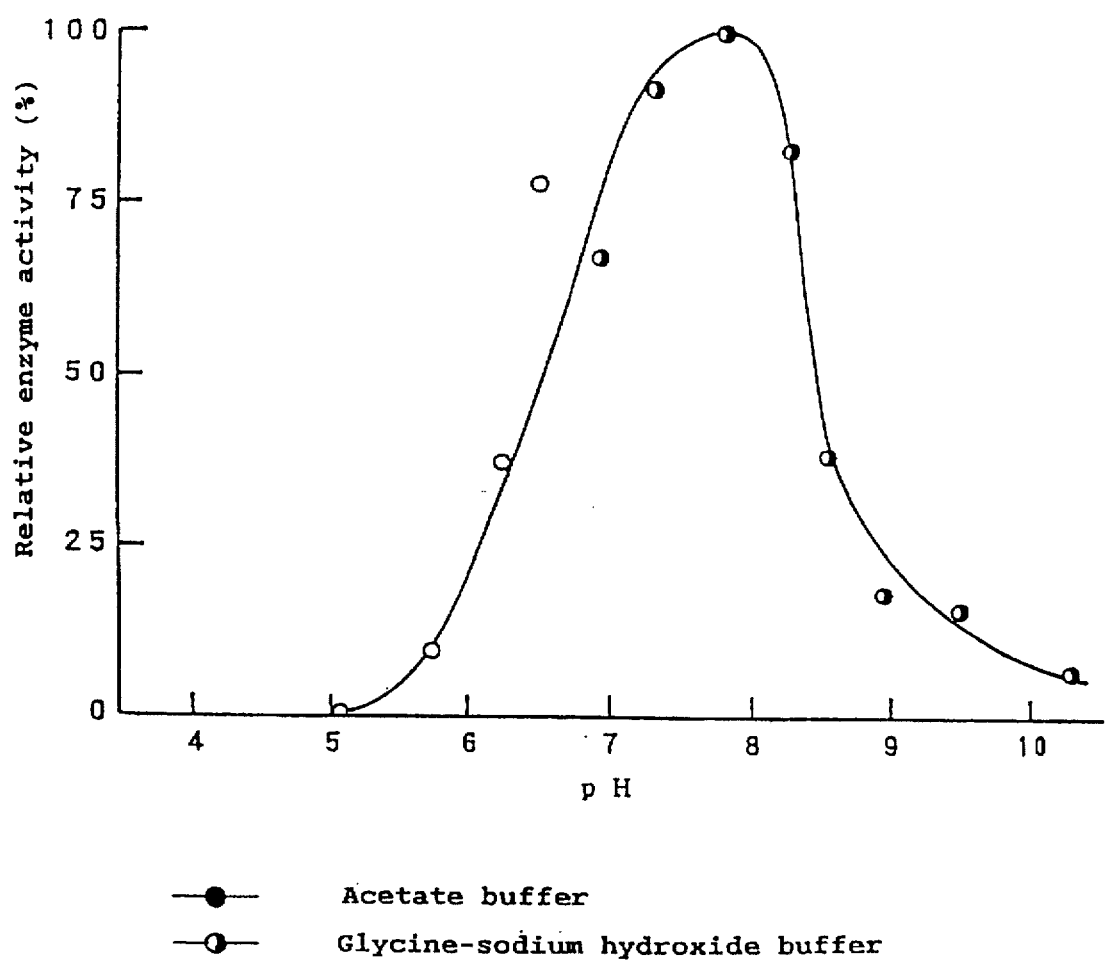
FIG. 6 shows the effect of pH on the activity of the maltose/trehalose conversion enzyme derived from *Pseudomonas putida* H262.
Figure 7:
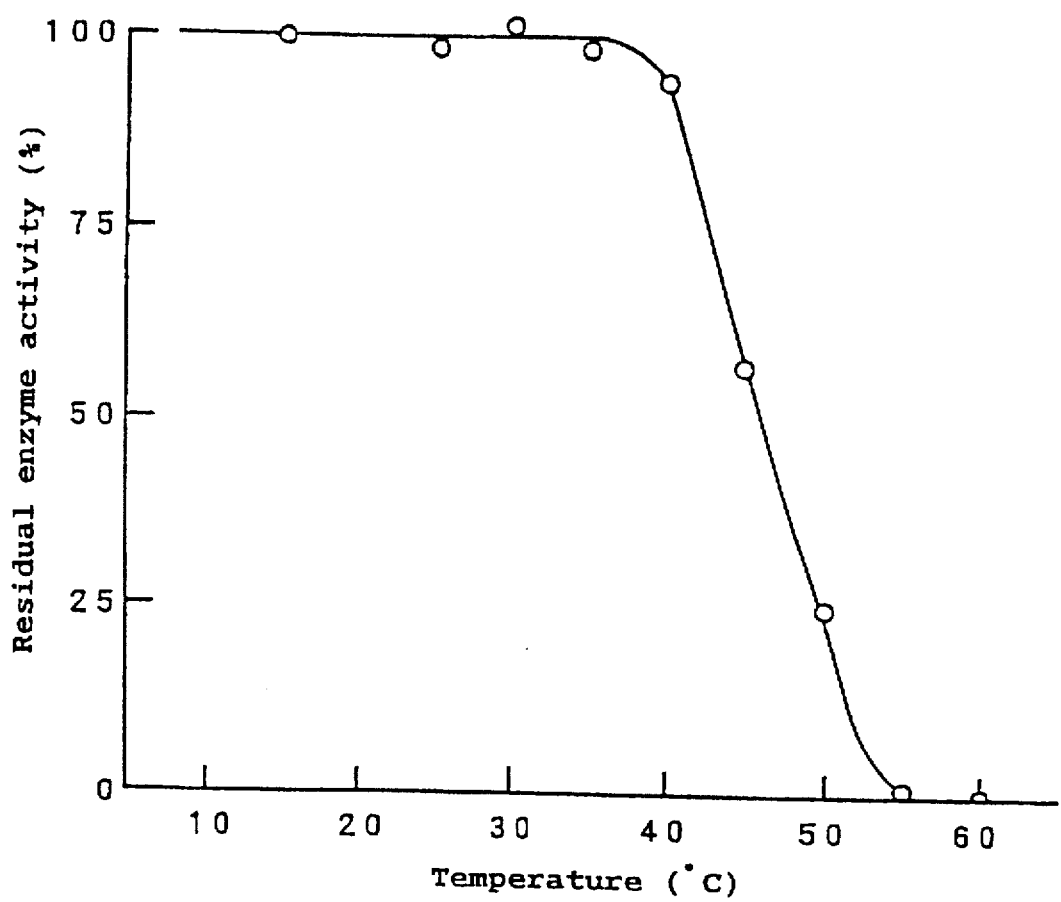
FIG. 7 shows the thermal stability of the maltose/trehalose conversion enzyme derived from *Pseudomonas putida* H262.
Figure 8:
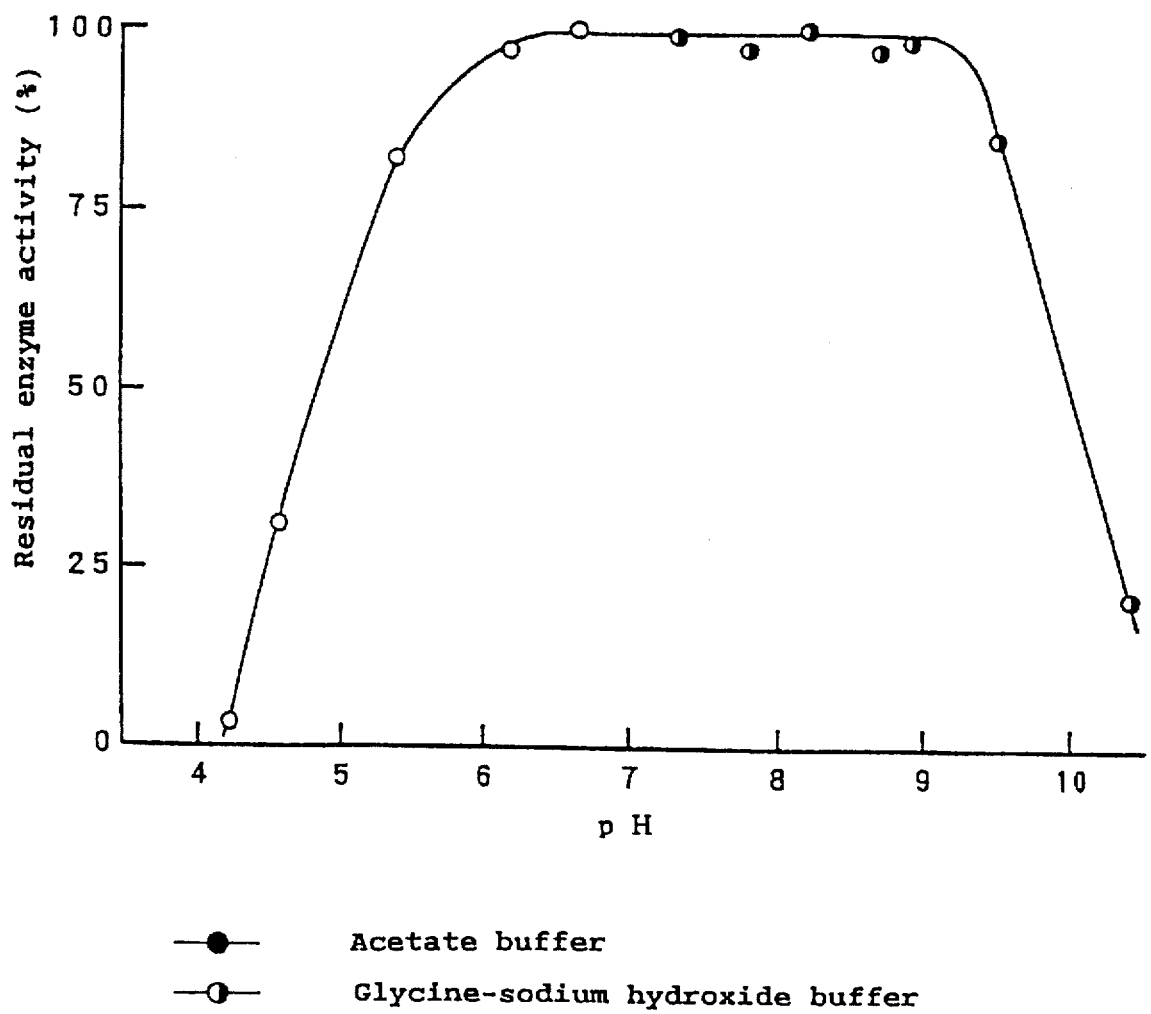
FIG. 8 shows the pH stability of the maltose/trehalose conversion enzyme derived from *Pseudomonas putida* H262.

Effects of temperature and pH on the activity of the enzyme were investigated in accordance with the assay method. The results were as shown in FIG. 5 for the effect of temperature and in FIG. 6 for the effect of pH. The optimum temperature of the enzyme was around 37° C. when allowed to react at pH7.0 for 60 minutes, while the optimum pH, about 7.3–8.3 when allowed to react at 35° C. for 60 minutes. The thermal stability of the enzyme was determined by incubating the enzyme in 50 mM phosphate buffer (pH7.0) at different temperatures for 60 minutes, cooling with water and assaying the residual activities. While the pH stability was determined by incubating at 35° C. for 60 minutes in 50 mM phosphate buffer with different pH levels, adjusting to pH7.0 and assaying the residual enzyme activities. Respective results were as shown in FIG. 7 for the thermal stability and in FIG. 8 for the pH stability. The thermal stability was up to about 40° C., while the pH stability, about pH6.0–9.5. The enzymatic activity was inhibited by 1 mM $Cu^{2+}$, $Hg^{2+}$ and 50 mM Tris-HCl buffer.

Experiment 12
Action on a variety of saccharides

A variety of saccharides were tested for feasibility as substrate for the purified enzyme from *Pseudomonas putida* H262 obtained in Experiment 10 in accordance with the method in Experiment 4 except that the reaction temperature was set to 35° C. As the result, like the enzyme from Pimelobacter species R48, the enzyme from *Pseudomonas putida* H262 acted on only maltose and trehalose to convert maltose to trehalose as well as to convert trehalose to maltose. It was found that the equilibrium point was declined to the trehalose side and therefore the conversion ratio from maltose into trehalose was high, in particular, about 70%.

Experiment 13
Effect of maltose concentration on the formation of trehalose

Maltose solutions, concentration of either 5%, 10%, 20% or 30%, were added and reacted at 35° C. and pH7.0 with 2 units/g maltose solid of a purified maltose/trehalose conversion enzyme obtained by the method in Experiment 10 and during the reaction the reaction liquids were periodically sampled and heated at 100° C. for 10 minutes to inactivate the enzyme.

The reaction liquids were determined for reducing power and saccharide composition similarly as in Experiment 6. The results were as shown in Table 8.

TABLE 8

| Maltose (%) | Reaction time (hour) | Reducing power (%) | Saccharide composition (%) | | |
|---|---|---|---|---|---|
| | | | Glucose | Maltose | Trehalose |
| | 0 | 50.3 | 0.0 | 100.0 | 0.0 |
| 5.0 | 2 | 43.8 | 0.8 | 88.0 | 11.2 |
| | 7 | 35.0 | 0.5 | 72.7 | 26.8 |
| | 24 | 17.2 | 0.5 | 41.8 | 57.7 |
| | 48 | 10.3 | 1.8 | 29.7 | 68.5 |
| 10.0 | 2 | 46.8 | 1.2 | 86.5 | 12.3 |
| | 7 | 34.6 | 1.4 | 64.9 | 33.7 |
| | 24 | 16.0 | 2.2 | 36.4 | 61.4 |
| | 48 | 14.8 | 3.7 | 26.5 | 69.8 |
| 20.0 | 2 | 44.9 | 0.7 | 86.6 | 12.7 |
| | 7 | 32.7 | 1.2 | 66.6 | 32.2 |
| | 24 | 21.0 | 2.6 | 35.8 | 61.6 |
| | 48 | 11.2 | 3.9 | 27.0 | 69.1 |
| 30.0 | 2 | 44.8 | 0.0 | 89.5 | 10.5 |
| | 7 | 38.2 | 0.6 | 72.5 | 26.9 |
| | 24 | 17.8 | 1.8 | 41.8 | 56.4 |
| | 48 | 12.9 | 3.9 | 29.6 | 66.5 |

As evident from the results in Table 8, the conversion from maltose into trehalose readily proceeded independently on the concentration of maltose as substrate marking a conversion rate of about 70%.

Experiment 14
Preparation of trehalose from maltose

Ten parts by weight of maltose commercialized by Hayashibara Biochemical Laboratories, Inc., Okayama, Japan, was dissolved in 40 parts by weight of water, added at 35° C. and pH7.0 with 2 units/g maltose solid of a purified maltose/trehalose conversion enzyme obtained by the method in Experiment 10, reacted for 48 hours and reacted at 100° C. for 10 minutes to enzyme. The resultant solution contained about 69% trehalose on dry solid basis. The solution was decolored with activated carbon, deionized and purified with ion exchanges of H- and OH-forms, concentrated to about 78%, added with 0.1% crystalline trehalose hydrate as seed crystal on dry solid basis and allowed to standing at ambient temperature overnight to effect crystallization. The resultant massecuite was separated and the crystals were sprayed with a minimum amount of water for washing, thus obtaining about 2.3 parts by weight of an extremely pure crystalline trehalose hydrate, purity of 99.7%.

Experiment 15
Production of enzyme

One hundred ml aliquots of a liquid culture medium consisting of 0.5 w/v % polypeptone, 0.1 w/v % yeast extract, 0.07 w/v % ammonium nitrate, 0.01 w/v % disodium hydrogen phosphate, 0.02 w/v % magnesium sulfate and water were adjusted to pH7.5, distributed in 500 ml flasks, autoclaved at 120° C. for 20 minutes for sterilization, cooled, inoculated with a stock culture of *Thermus aquaticus* (ATCC33923) and cultivated at 60° C. and 200 rpm for 24 hours under shaking conditions to obtain a seed culture.

About 20 liter aliquots of a fresh preparation of the same liquid culture medium as above were placed in two 30 liter fermenters, sterilized by heating, cooled to 60° C., inoculated with 1 v/v % seed culture and cultivated at 60° C. for about 24 hours under aeration and agitation conditions while retaining at 60° C. and pH6.5–8.0.

The activity of maltose/trehalose conversion enzyme in the culture was about 0.35 units/ml. A portion of the culture was sampled and centrifugally separated into cells and supernatant and the cells were then suspended in 50 mM phosphate buffer (pH7.0) to give the same volume as that of the sampled culture, followed by determining the enzymatic activities in the cell suspension and supernatant, revealing that about 0.33 units/ml of enzyme activity was found in the cell suspension, while about 0.02 units/ml, in the supernatant. The enzymatic activities were determined at 60° C.

Experiment 16
Purification of enzyme

The culture obtained in Experiment 15 was centrifugally separated to collect the cells, about 0.28 kg wet weight, which were then suspended in 10 mM phosphate buffer (pH7.0). The cell suspension, about 1.9 liters, was subjected to "MODEL US300", a ultrasonic cell disrupter commercialized by Nippon Seiki Co., Ltd., Niigata, Japan, to disrupt the cells and the resultant was centrifuged at 15,000 rpm for 30 minutes to obtain about 1.8 liters of a supernatant. The supernatant was added with ammonium sulfate to give a saturation degree of 0.7, allowed to standing at 4° C. overnight and centrifuged, followed by recovering the sediment.

The sediment was dissolved in 10 mM phosphate buffer (pH7.0), dialyzed against a fresh preparation of the same buffer for 24 hours and centrifuged to remove insoluble substances. The dialyzed solution, about 1,560 ml, was divided into three portions which were then separately applied to ion exchange column chromatography on 530 ml "DEAE TOYOPEARL 650".

The maltose/trehalose conversion enzyme according to the present invention, which had been adsorbed on "DEAE TOYOPEARL", was eluted therefrom with a fresh preparation of the same buffer but additionally containing sodium chloride. The enzymatically active fractions thus obtained were recovered, dialyzed against a fresh preparation of the same buffer but additionally containing 1M ammonium sulfate and subjected to a hydrophobic column chromatography on 380 ml "BUTYL TOYOPEARL 650". The maltose/trehalose conversion enzyme which had been adsorbed in the column was eluted therefrom under a linear gradient decreasing from 1M to 0M for ammonium sulfate, followed by recoverying the enzymatically active fractions.

The fractions were applied to gel filtration chromatography on 380 ml "TOYOPEARL HW-55S" and the enzymatically active fractions were recovered.

Thereafter the fractions were subjected to ion exchange chromatography on 1.0 ml "MONO Q HR5/5" commercialized by Pharmacia LKB, Uppsala, Sweden, and eluted under a linear gradient increasing 0.1M to 0.35M for sodium chloride, followed by recovering the enzymatically active fractions. The enzymatic activities, specific activities and yields in respective purification stages were as shown in Table 9.

After checking the purity of the purified enzyme on polyacrylamide gel electrophoresis, gel concentration of 5 w/v %, it gave a single band of protein confirming that it was homogenous and highly pure.

TABLE 9

| Purification stage | Enzymatic activity (units) | Specific activity (units/mg protein) | Yield (%) |
|---|---|---|---|
| Supernatant of disrupted culture | 8,800 | 0.10 | 100 |
| Liquid after salting out by ammonium sulfate and dialysis | 8,710 | 0.16 | 99.0 |
| Eluate of ion exchange column chromatography | 5,690 | 2.5 | 64.7 |
| Eluate of hydrophobic column chromatography | 2,050 | 17.6 | 23.3 |
| Eluate of gel filtration column chromatography | 937 | 113 | 10.6 |
| Eluate of ion exchange column chromatography | 467 | 135 | 5.3 |

Experiment 17
Properties of enzyme

A purified maltose/trehalose conversion enzyme obtained by the method in Experiment 16 was subjected to SDS-polyacrylamide gel electrophoresis, gel concentration of 7.5 w/v %, and determined for molecular weight by comparing with those of the molecular weight markers commercialized by Japan Bio-Rad Laboratories, Tokyo, Japan, which had been electrophoresed on the same gel, revealing that the molecular weight of the enzyme was about 100,000–110,000 daltons.

The purified maltose/trehalose conversion enzyme was electrophoresed on polyacrylamide gel using 2 w/v % Ampholine commercialized by Pharmacia LKB, Uppsala, Sweden, and the pH levels of the protein bands and gel were determined, revealing that the isoelectric point of the enzyme was about pI3.8–4.8.

Figure 9:
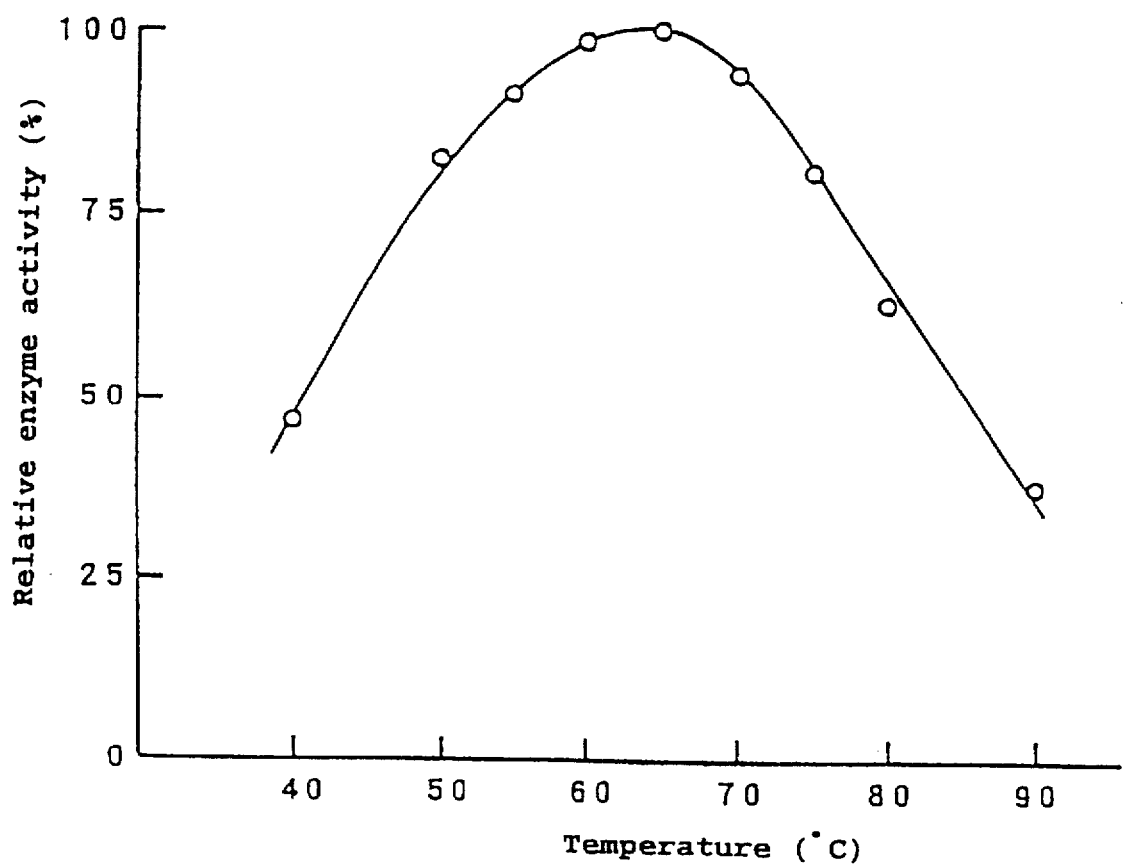
FIG. 9 shows the effect of temperature on the activity of the maltose/trehalose conversion enzyme derived from *Thermus aquaticus* (ATCC33923).
Figure 10:
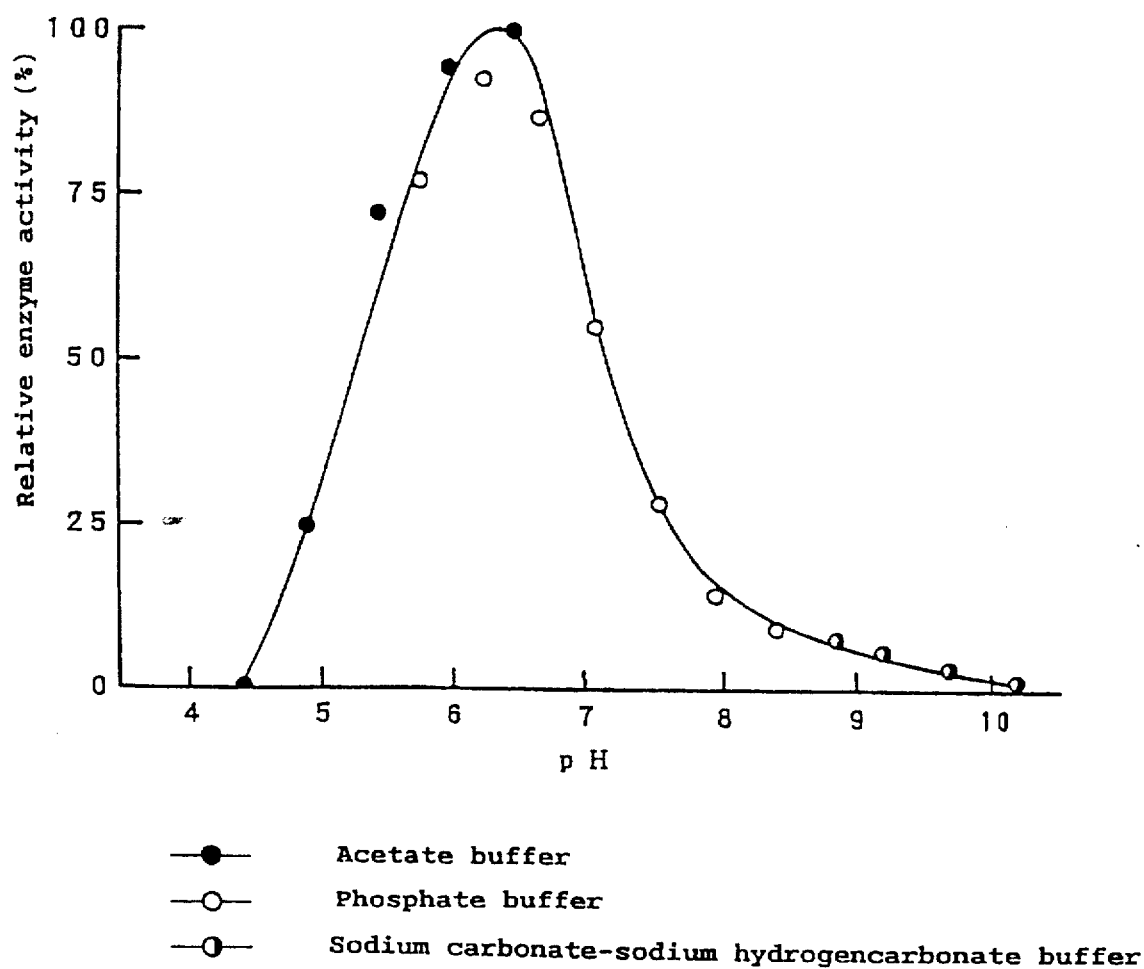
FIG. 10 shows the effect of pH on the activity of the maltose/trehalose conversion enzyme derived from *Thermus aquaticus* (ATCC33923).
Figure 11:
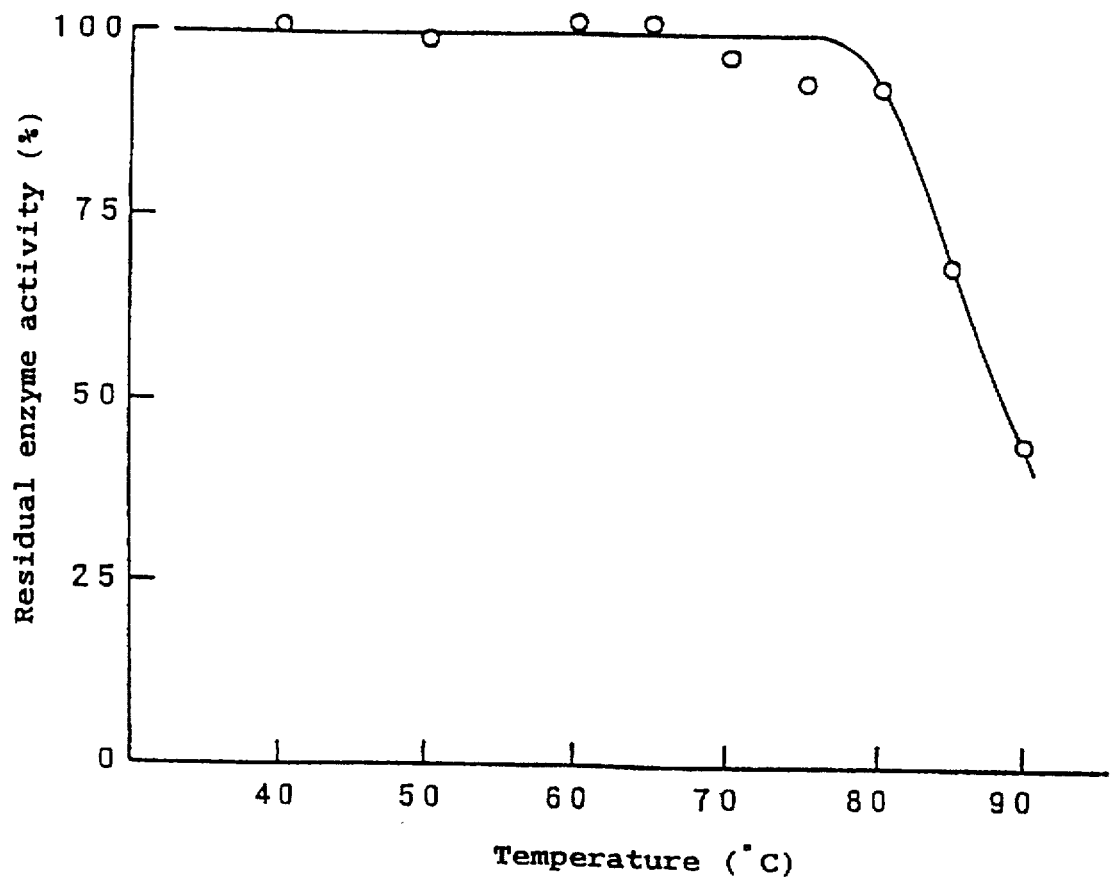
FIG. 11 shows the thermal stability of the maltose/trehalose conversion enzyme derived from *Thermus aquaticus* (ATCC33923).
Figure 12:
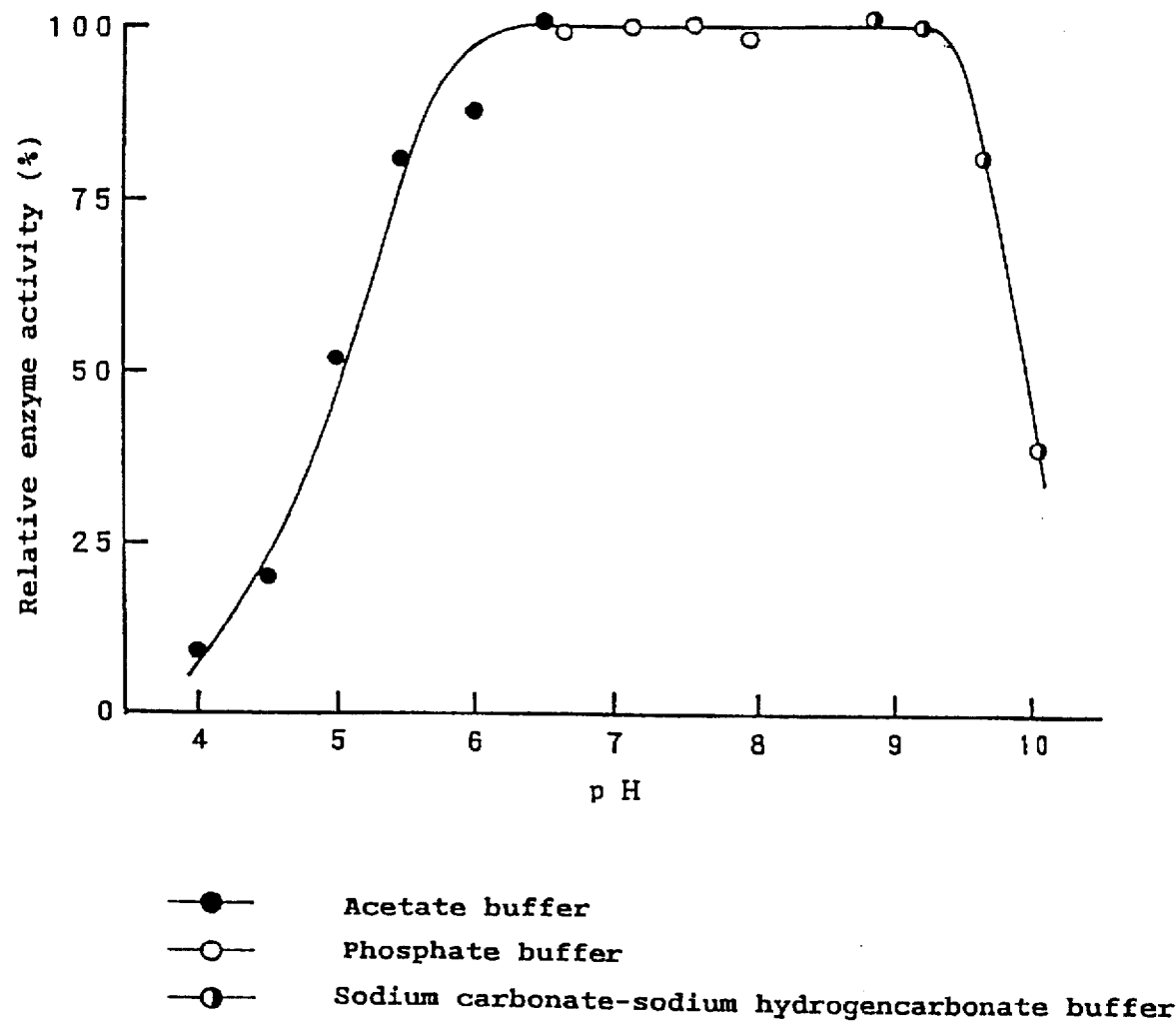
FIG. 12 shows the pH stability of the maltose/trehalose conversion enzyme derived from *Thermus aquaticus* (ATCC33923).

Effects of temperature and pH on the activity of the enzyme were investigated in accordance with the assay method. The results were as shown in FIG. 9 for the effect of temperature and in FIG. 10 for the effect of pH. The optimum temperature of the enzyme was around 65° C. when allowed to react at pH7.0 for 60 minutes, while the optimum pH, about 6.0–6.7 when allowed to react at 60° C. for 60 minutes. The thermal stability of the enzyme was determined by incubating the enzyme in 50 mM phosphate buffer (pH7.0) at different temperatures for 60 minutes, cooling with water and assaying the residual activities. While the pH stability was determined by incubating at 60° C. for 60 minutes in 50 mM phosphate buffer with different pH levels, adjusting to pH7.0 and assaying the residual enzyme activities. Respective results were as shown in FIG. 11 for the thermal stability and in FIG. 12 for the pH stability. The thermal stability was up to about 80° C., while the pH stability, about pH5.5–9.0. The enzymatic activity was inhibited by 1 mM $Cu^{2+}$, $Hg^{2+}$ and 50 mM Tris-HCl buffer.

Experiment 18
Action on a variety of saccharides

A variety of saccharides were tested for feasibility as substrate for the purified enzyme from Thermus aquaticus (ATCC33923) obtained in Experiment 16 in accordance with the method in Experiment 4 except that the reaction temperature was set to 50° C. As the result, like the enzymes from Pimelobacter species R48 and Pseudomonas putida H262, the enzyme from Thermus aquaticus (ATCC33923) acted on only maltose and trehalose to convert maltose to trehalose as well as to convert trehalose into maltose. It was found that the equilibrium point was declined to the trehalose side and therefore the conversion ratio from maltose into trehalose was high, in particular, 70% or higher.

Experiment 19
Effect of maltose concentration on the formation of trehalose

Maltose solutions, concentration of either 2.5%, 5%, 10%, 20% or 40%, were added and reacted at 60° C. and pH6.5 with 2 units/g maltose solid of a purified maltose/trehalose conversion enzyme obtained by the method in Experiment 16 and after a lapse of 72 hours the reaction liquids were sampled and heated at 100° C. for 30 minutes to inactivate the enzyme. The reaction liquids were determined for reducing power and saccharide composition similarly as in Experiment 6. The results were as shown in Table 10.

TABLE 10

| Maltose (%) | Reaction time (hour) | Reducing power (%) | Saccharide composition (%) | | |
|---|---|---|---|---|---|
| | | | Glucose | Maltose | Trehalose |
| | 0 | 50.4 | 0.0 | 100.0 | 0.0 |
| 2.5 | 72 | 16.3 | 4.5 | 25.2 | 70.3 |
| 5.0 | 72 | 15.9 | 4.4 | 25.6 | 70.0 |
| 10.0 | 72 | 16.0 | 4.7 | 25.6 | 69.7 |
| 20.0 | 72 | 16.6 | 4.4 | 26.2 | 69.4 |
| 40.0 | 72 | 16.8 | 5.0 | 26.4 | 68.6 |

As evident from the results in Table 10, the conversion from maltose into trehalose readily proceeded independently on the concentration of maltose as substrate marking a conversion rate of about 70%.

Experiment 20
Effect of temperature of the formation of trehalose

Maltose solutions, concentration of 20% each, were adjusted to pH6.5, added with 2.5 units/g maltose solid of a purified maltose/trehalose conversion enzyme from Thermus aquaticus (ATCC33923) obtained by the method in Experiment 16 and reacted at either 40° C., 50° C., 60° C.

or 70° C. and during the reaction the reaction liquids were periodically sampled and heated at 100° C. for 30 minutes to inactivate the enzyme. The enzymatic reaction liquids were analyzed on HLPC for saccharide composition similarly as in Experiment 6. The trehalose contents at respective reaction temperatures and times were as shown Table 11.

TABLE 11

| Reaction time | Trehalose content (%) | | | |
|---|---|---|---|---|
| (hour) | 40° C. | 50° C. | 60° C. | 70° C. |
| 4 | 45.0 | 55.7 | 56.8 | 50.3 |
| 8 | 61.0 | 67.3 | 64.3 | 58.5 |
| 24 | 79.1 | 76.5 | 71.1 | 64.3 |
| 48 | 80.7 | 76.9 | 70.2 | 62.8 |
| 72 | 80.0 | 76.4 | 68.5 | 60.2 |

As evident from the results in Table 6, although the formation rate for trehalose was more readily at a lower temperature, at 40° C., the conversion from maltose into trehalose readily proceeded marking a conversion rate of about 80%.

Experiment 21
Production and Properties of maltose/trehalose conversion enzyme from other microorganisms Among conventional microorganisms, the specified microorganisms which had been confirmed for production of the maltose/trehalose conversion enzyme according to the present invention were cultivated in flasks for 48 hours in accordance with the method in Experiment 15. Respective cultures were checked for enzymatic activity and then subjected to cell disrupter in accordance with the method in Experiment 16 and the supernatants were dialyzed to obtain partially-purified enzymes which were then investigated for properties in accordance with the method in Experiment 17. The results were as shown in Table 12.

After testing the partially-purified enzymes derived from these conventional microorganisms of the genus Thermus for action on a variety of saccharides in accordance with the method in Experiment 18, it was found that like the enzyme derived from *Thermus aquaticus* (ATCC33923), they acted on only maltose and trehalose to form trehalose from maltose as well as to form maltose from trehalose.

other microorganisms beared approximately the same properties as those of *Thermus aquaticus* (ATCC33923) and a high heat resistance.

Experiment 22
Physicochemical properties of trehalose preparations

A high-purity trehalose prepared by the method in Experiment 8 was tested for physicochemical properties. The melting point was 97.0° C.; specific rotation [alpha]$_D^{20}$, +199° (c=5); heat of melting, 57.8 KJ/mole; and solubility as anhydrous substance, 77.0 g in 25° C. water. These physical values were in good agreement with those of a simultaneously tested commercially-available crystalline trehalose hydrate, a product of Wako Pure Chemical Industries, Ltd., Osaka, Japan.

Experiment 23
Test for assimilation in vivo

In accordance with the method reported by Atsuji et al., *Rinsho Eiyo (Clinical Nutrition)*, Vol.41, No.2, pp.200–208 (1972), 30 g of the high-purity trehalose, purity of 99.8%, prepared in Experiment 8 was prepared into 20 w/v % aqueous solution and orally administered to healthy three men, age of 26, 27 and 30 years, after which their bloods were periodically sampled and measured for blood sugar and insulin levels. Glucose was used as control. As the result, trehalose behaved similarly as glucose did, and the blood sugar and insulin levels reached maxima about 0.5–1 hour after administration. It was confirmed that trehalose was readily digested and absorbed and then metabolized and utilized as energy source. Thus the trehalose and saccharide containing the same are suitable as saccharide source for energy supplement.

Experiment 24
Acute toxicity test

An acute toxicity test was conducted on a high-purity trehalose prepared in Example A-6, where it was orally administered in mice. As the result, trehalose was a low toxic substance causing no death even in the possible highest dose. Thus its LD50 would be briefly 50 g/kg or higher.

Experiment 25
Effect of maltose concentration on the formation of trehalose by cultivation

TABLE 12

| Microorganism | Activity (unit/ml) | Optimum Temperature | Optimum pH | Thermal stability | pH Stability |
|---|---|---|---|---|---|
| *Thermus aquaticus* (ATCC27634) | 0.30 | around 65° C. | about 6.5–6.8 | up to about 80° C. | about 5.5–9.5 |
| *Thermus ruber* (ATCC35948) | 0.26 | around 50° C. | about 6.0–7.0 | up to about 50° C. | about 5.5–10.0 |
| Thermus species (ATCC43815) | 0.25 | around 65° C. | about 6.0–6.5 | up to about 80° C. | about 5.5–9.5 |
| Pimelobacter species R48 in Experiments 1–3 | 0.55 | around 20° C. | about 7.0–8.0 | up to about 30° C. | about 6.0–9.0 |
| *Pseudomonas putida* H262 in Experiments 12–14 | 0.12 | around 37° C. | about 7.3–8.3 | up to about 40° C. | about 6.0–9.5 |
| *Thermus aquaticus* (ATCC33923) in Experiments 18–20 | 0.35 | around 65° C. | about 6.0–6.7 | up to about 80° C. | about 5.5–9.5 |

Also was found that the maltose/trehalose conversion enzyme from *Thermus ruber* (ATCC35948) was lower in optimum temperature and thermal stability that that from *Thermus aquaticus* (ATCC33923) but the enzymes from The effect of maltose concentration on trehalose yield in cultures were tested by cultivating different types of microorganisms capable of producing maltose/trehalose conversion enzyme in a nutrient culture medium with 2–20% maltose. In particular, in the case of Pimelobacter species R48 (FERM BP-4315), cultivation was carried out in fermenter at 27° C. for 72 hours similarly as in Experiment 1 except that in the nutrient medium 2.0 w/v % glucose was replaced with 2–20 w/v % maltose which had been separately sterilized, added with 0.1 v/v % "TWEEN 40", a surface-active agent containing polyoxyethylene sorbitan palmitate commercialized by Wako Pure Chemical Industries, Ltd., Osaka, Japan, and cutlviated for additional 24 hours. In the case of *Thermus aquaticus* (ATCC33923), cultivation was carried out in fermenter at 60° C. for 24 hours similarly as in Experiment 15 except that a nutrient culture medium with 2–20 w/v % maltose which had been separately sterilized was used, added with 0.1 v/v % "TWEEN 40", and cultivated for additional 24 hours. The cultures were centrifugally separated and the supernatants were determined for trehalose content (mg/ml) on HPLC. The results were as shown in Table 13.

As evident from the results in Table 13, it was found that a maltose concentration of 20 w/v % or less, desirably, 15 w/v % or less, more desirably, 5–10 w/v %, was favorable in the production of trehalose because it maked an elevated trehalose yield.

TABLE 13

| Microorganism | Maltose concentration (w/v %) | Trehalose concentration (mg/ml) |
|---|---|---|
| Pimelobacter species R48 (FERM BP-4315) | 2 | 3.1 |
| | 5 | 20.6 |
| | 10 | 30.4 |
| | 15 | 9.8 |
| | 20 | 2.7 |
| Thermus aquaticus (ATCC33923) | 2 | 4.2 |
| | 5 | 22.5 |
| | 10 | 34.6 |
| | 15 | 8.1 |
| | 20 | 2.0 |

The following Examples A are to illustrate a process to produce trehalose or saccharide containing the same using maltose/trehalose conversion enzymes according to the present invention, while Examples B are to illustrate compositions which contain either of these.

EXAMPLE A-1

Potato starch in about 10% suspension (pH5.5) was added with 2 units/g starch solid of "SPITASE HS", an alpha-amylase commercialized by Nagase Biochemical Ltd., Kyoto, Japan, gelatinized and liquefied under stirring and heating conditions, immediately autoclaved at 120° C. for 20 minutes and adjusted to 50° C. and pH5.0. The resultant was added with 20 units/g starch solid of beta-amylase commercialized by Nagase Biochemical Ltd., Kyoto, Japan, along with 500 units/g starch solid of isoamylase commercialized by Hayashibara Biochemical Laboratories, Inc., Okayama, Japan, reacted for 24 hours, heated to 95° C. to inactivate the enzymes, filtered and decolored to obtain a saccharide liquid with a maltose content of about 92%. A nutrient culture medium was prepared in accordance with the method in Experiment 1 except that in place of 2.0 w/v % glucose the above saccharide liquid as saccharide source was separately sterilized and incorporated thereto in an amount of 10 w/v % in terms of solid, placed in fermenter, inoculated with 1 v/v % seed culture of Pimelobacter species R48 (FERM BP-4315), a microorganism capable of producing maltose/trehalose conversion enzyme, cultivated at 27° C. for 72 hours under aeration and agitation conditions similarly as in Experiment 1, added with 0.2 v/v % "TRITON X-100", a surface-active agent containing alkylphenol polyoxyethylene ether commercialized by Wako Pure Chemical Industries, Osaka, Japan, and cultivated for additional 24 hours. The culture was filtered to remove insoluble substances and the resultant filtrate was heated to 95° C. to inactive the enzyme, concentrated, decolored with activated carbon, filtered, deionized and purified with ion exchanges of H- and OH-forms in usual manner and further concentrated to about 75%, thus obtaining a syrup product in the yield of about 65% on dry solid basis. The product, which contained about 44% trehalose on dry solid basis, can be favorably used as sweetener, taste improving agent, stabilizer and shape imparting agent in a variety of compositions including food products, cosmetics and medicines because it bears a mild sweetness and appropriate viscosity and moisture retaining ability.

EXAMPLE A-2

A filtrate of culture obtained by the method in example A-1 was exposed at pH5.0 and 50° C. for 24 hours to 10 units/g solid of "GLUCOZYME", a glucoamylase commercialized by Nagase Biochemical Ltd., Kyoto, Japan, heated to inactivate the enzyme, decolored, deionized and purified to obtain a saccharide liquid which was then subjected as starting saccharide solution to ion exchange column chromatography using "XT-1016", a strongly-acidic cation exchange of sodium form, crosslinkage degree of 4%, commercialized by Tokyo Organic Chemical Industries, Ltd., Tokyo, Japan, so as to elevate the trehalose content. The ion exchange was packed in 4 jacketed-stainless steel columns, inner diameter of 5.4 cm each, which were then cascaded to give a total length of 20 m. While keeping the temperature inside the columns at 60° C., they were added with 5 v/v % saccharide liquid against the resin and injected with 60° C. water at SV0.15 to remove glucose by fractionation, followed by recovering trehalose-rich fractions. The fractions were purified, concentrated, dried in vacuo and pulverized to obtain a powder product with a high trehalose content in the yield of about 35% on dry solid basis. The product, which contains about 97% trehalose on dry solid basis, can be favorably used as sweetener, taste improving agent, quality improving agent, stabilizer and shape imparting agent in a variety of compositions including food products, cosmetics and medicines because it bears an extremely low reducing power and mild and gentle sweetness.

EXAMPLE A-3

A trehalose-rich fraction obtained by the method in Example A-2 was decolored with activated carbon, deionized and purified with ion exchanges in usual manner, concentrated to about 70%, placed in a crystallizer, added with about 2% crystalline trehalose hydrate as seed crystal and gradually cooled to obtain a massecuite with a crystallization degree of about 45%. The massecuite was then sprayed at 150 kg/cm$_2$ through a high-pressure nozzle provided at the top of a drying tower, while supplying downwards 85° C. air from the top of the drying tower and collecting the resultant crystalline powder on a conveyer of metal net provided at the bottom of the drying tower. The crystalline powder was gradually moved and transferred outside the drying tower while supplying 45° C. air upwardly through the conveyer. The crystalline powder was placed in ageing tower where the powder was aged for 10 hours in a stream of warmed air to complete crystallization and drying, thus obtaining a crystalline trehalose hydrate powder in the yield of about 90% against the starting trehalose-rich fraction on dry solid basis. The product can be favorably used as sweetener, taste improving agent and stabilizer in a variety of compositions including food products, cosmetics and medicines because it is substantially free of hygroscopicity and easily handleable.

EXAMPLE A-4

A trehalose-rich fraction obtained by the method in Example A-2 was purified similarly as in Example A-3, placed in evaporator and boiled in vacuo to obtain a syrup with a moisture content of about 3.0%. The syrup was placed in crystallizer, added with 1% anhydrous crystalline trehalose as seed crystal on dry solid basis, crystallized at 120° C. while stirring, distributed in aluminum baths and allowed to stand at 100° C. for 6 hours for crystallization and ageing, thus obtaining solid products in block form. The products were the subjected to cutting machine and dried on fluidized bed to obtain an anhydrous crystalline trehalose powder, moisture content of about 0.3%, in the yield of about 85% against the starting trehalose-rich fraction on dry solid basis. The product can be favorably used as white powdered sweetener with a mild sweetness in a variety of compositions including food products, cosmetics and medicines, as well as desiccant for food products, cosmetics, medicines and materials and intermediates therefor.

EXAMPLE A-5

Cornstarch in 33% suspension was added with 0.1% calcium carbonate, adjusted to pH 6.5, added with 0.2% "TERMAMYL 60L", an alpha-amylase commercialized by Novo Industri AS, Copenhagen, Denmark, on dry solid basis, and reacted at 95° C. for 15 minutes. The reaction liquid was autoclaved at 120° C. for 30 minutes, cooled to 55° C., added with 500 units/g starch solid of isoamylase commercialized by Hayashibara Biochemical Laboratories, Inc., Okayama, Japan, along with 30 units/g starch solid of beta-amylase commercialized by Nagase Biochemical Ltd., Kyoto, Japan, reacted for 48 hours, heated to 95° C. to inactivate the enzymes, filtered and decolored to obtain a saccharide liquid with a maltose content of about 84%. A nutrient culture medium was prepared in accordance with the method in Experiment 9 except that the above saccharide liquid as saccharide source was separately sterilized and supplemented thereto in an amount of 10 w/v % in terms of solid, placed in fermenter, inoculated with 1 v/v % seed culture of Pseudomonas putida H262 (FERM BP-4579), a microorganism capable of producing maltose/trehalose conversion enzyme, cultivated at 27° C. for 48 hours under aeration and agitation conditions similarly as in Experiment 9, added with 0.2 v/v % "TWEEN 40" and cultivated for additional 48 hours. The culture was filtered to remove insoluble substances and the resultant filtrate was heated to 95° C. to inactivate the enzyme, concentrated, decolored with activated carbon, filtered, deionized and purified with ion exchange of H- and OH-forms in usual manner and further concentrated to about 70%, thus obtaining a syrup product in the yield of about 50% on dry solid basis. The product, which contained about 64% trehalose on dry solid basis, can be favorably used in a variety of compositions including food products, cosmetics and medicines because it bears a decreased reducing power, mild sweetness, appropriate viscosity and moisture-retaining ability.

EXAMPLE A-6

A syrup obtained by the method in Example A-5 was concentrated to about 80%, placed in crystallizer, added with 1% crystalline trehalose hydrate as seed crystal and gradually cooled while stirring to effect crystallization. The crystals in the resultant massecuite were separated in basket-type centrifuge and sprayed with a minimum amount of water for washing to obtain a high-purity crystalline trehalose hydrate in the yield of about 20% on dry solid basis. The product, which bears physicochemical properties similar to those in Experiment 22, can be favorably used as sweetener, taste improving agent, quality improving agent and stabilizer in a variety of compositions including food products, cosmetics and medicines. The product can be also feasible in industrial reagent and chemical material.

EXAMPLE A-7

Cornstarch in 10% suspension (pH5.5) was added with 2 units/g starch solid of "SPITASE HS", a commercially-available alpha-amylase, gelatinized and liquefied unders stirring and heating conditions, immediately autoclaved at 120° C. for 20 minutes and adjusted to 55° C. and pH5.0. The resultant was added with 300 units/g starch solid of isoamylase commercialized by Hayashibara Biochemical Laboratories, Inc., Okayama, Japan, along with 20 units/g starch solid of beta-amylase commercialized by Nagase Biochemical Ltd., Kyoto, Japan, reacted for 24 hours, heated to 95° C. to inactivate the enzymes, filtered and decolored to obtain a saccharide liquid with a maltose content of about 92%. A nutrient culture medium was prepared in accordance with the method in Experiment 15 except that the above saccharide liquid was separately sterilized and supplemented thereto as saccharide source in an amount of 10 w/v % on dry solid basis, placed in fermenter, inoculated with 1 v/v % seed culture of Thermus aquaticus (ATCC33923), a microorganism capable of producing maltose/trehalose conversion enzyme, cultivated at 60° C. for 40 hours similarly as in Experiment 15, added with 0.1 v/v % "TRITON X-100" along with 50 mg/l culture of egg white lysozyme and cultivated for additional 16 hours. The culture was filtered to remove insoluble substances and the resultant filtrate was heated to 95° C. to inactivate the enzyme, concentrated, decolored with activated carbon, filtered, deionized and purified with ion exchanges of H- and OH-form in usual manner and further concentrated to about 70%, thus obtaining a syrup product in the yield of about 55% on dry solid basis. The product, which contains about 68% trehalose on dry solid basis, can be favorably used as sweetener, taste improving agent, stabilizer and shape imparting agent in a variety of compositions including food products, cosmetics and medicines because it bears a mild sweetness, appropriate viscosity and moisture retaining ability.

EXAMPLE A-8

A syrup obtained by the method in Example A-7 was concentrated to about 85%, placed in crystallizer, added with 1% seed crystal, distributed in baths, allowed to stand at 20° C. for 4 days to effect crystallization and solidification, pulverized with cutting machine and dried to obtain a crystalline mixture powder containing trehalose in the yield of about 95% on dry solid basis. The product can be favorably used as sweetener, taste improving agent, quality improving agent and stabilizer in a variety of compositions including food pro- ducts, cosmetics and medicines because it is substantially non-hygroscopic and very handleable.

EXAMPLE A-9

A syrup obtained by the method in Example A-7 was concentrated to about 80%, placed in crystallizer and crystallized similarly as in Example A-6 and the resultant crystals were separated to obtain a high-purity crystalline trehalose hydrate in the yield of about 20% on dry solid basis. The product, which, like the product in Example A-6, bears physicochemical properties similar to those in Experiment 22, can be favorably used in a variety of compositions including food products, cosmetics and medicines, as well as in industrial or chemical reagent and material.

EXAMPLE B-1
Sweetener

One part by weight of a crystalline trehalose hydrate powder obtained by the method in Example A-3 was mixed to homogeneity with 0.01 part by weight of "ALPHA G SWEET", an alpha-glycosyl stevioside commercialized by Toyo Sugar Refining Co., Ltd., Tokyo, Japan, and 0.01 part by weight of "ASPARTAME", an L-aspartyl-L-phenylalanine methyl ester commercialized by Ajinomoto Inc., Tokyo, Japan, and the mixture was fed to granulater to obtain a granular product of sweetener. The product has a superior quality for sweetness and a sweetening power about 2-fold stronger than that of sucrose and its calorie is about one half of that of sucrose per sweetening power. Since the product is superior in stability and free of decomposition of the ingredients which exhibit high sweetening powers, it is suitable as low-calorie sweetener to sweeten low-calorie food products for persons with diabetes or obesity whose calorie intakes are restricted. Further the product is suitable to sweeten food products which are suppressive on dental caries because it induces less formation of acids and insoluble glucans by dental caries-causative microorganisms.

EXAMPLE B-2
Hard candy

One hundred parts by weight of 55% sucrose solution was mixed with 30 parts by weight of a syrup containing trehalose obtained by the method in Example A-1 while heating, concentrated by heating in vacuo to a moisture content lower than 2%, admixed with one part by weight of citric acid and appropriate amounts of lemon flavor and coloring agent and shaped in conventional manner to obtain products. The products are high-quality hard candies which are crisp, superior in taste and free of crystallization of sucrose and deformation.

EXAMPLE B-3
Chocolate

Forty parts by weight of cacao paste, 10 parts by weight of cacao butter, 30 parts by weight of sucrose, 20 parts by weight of a high-purity crystalline trehalose hydrate obtained by the method in Example A-6 were mixed, fed to refiner to reduce particle sizes and kneaded in conche at 50° C. for 2 days. During the kneading, 0.5 parts by weight of lecithin was added and sufficiently dispersed to homogeneity. The resultant was adjusted to 31° C. with thermocontroller, distributed in molds immediately before solidification of the butter, deaerated with vibrator and passed through 10° C. cooling tunnel over 20 minutes for solidification. The contents were taken out from the molds and packaged to obtain products. The products are free of hygroscopicity but have a superior color, gloss and texture and smoothly dissolves in the mouth to give a gentle sweetness and a mild flavor and taste.

EXAMPLE B-4
Chewing gum

Three parts by weight of gum base was softened by melting while heating, added with 4 parts by weight of sucrose and 3 parts by weight of a crystalline trehalose hydrate powder obtained by the method in Example A-3, mixed with appropriate amounts of flavoring and coloring agents, kneaded with roller in conventional manner, shaped and packaged to obtain a product. The product is a chewing gum with a superior texture, flavor and taste.

EXAMPLE B-5
Sweetened condensed milk

In 100 parts by weight of fresh milk was dissolved 3 parts by weight of a syrup containing trehalose obtained by the method in Example A-5 and one part by weight of sucrose and the mixture was pasteurized by heating on plate heater, concentrated to 70% and sterilely canned to obtain a products. The product, which has a mild sweetness and a superior flavor and taste, can be favorably used as seasoning in infants' foods, fruits, coffee, cocoa and tea.

EXAMPLE B-6
Beverage containing lactic acid bacteria

One hundred and seventy-five parts by weight of defatted milk, 8 parts by weight of a powder with a high trehalose content obtained by the method in Example A-2 and 50 parts by weight of a powder with high lactosucrose content as disclosed in Japanese Patent Kokai No.281,795/92 were dissolved in 1,200 parts by weight of water, pasteurized at 65° C. for 30 minutes, cooled to 40° C., added with 30 parts by weight of starter and cultivated at 37° C. for 8 hours in conventional manner to obtain a beverage which contained lactic acid bacteria. The product is superior in taste and flavor. The oligosaccharides in the product stably maintain lactic acid bacteria and stimulate the growth of bifidobacteria.

EXAMPLE B-7
Powdered juice

Thirty three parts by weight of orange juice powder prepared by spray drying was mixed by stirring to homogeneity with 50 parts by weight of a high-purity crystalline trehalose hydrate obtained by the method in Example A-6, 10 parts by weight of sucrose, 0.65 parts by weight of anhydrous citric acid, 0.1 part by weight of malic acid, 0.1 part by weight of L-ascorbic acid, 0.1 part by weight of sodium citrate, 0.5 parts by weight of pullulan and an appropriate amount of powdered flavoring agent, cut into fine powder, fed to fluidized-bed granulater, sprayed with a high-trehalose content syrup as binder obtained by the method in Example A-5 at an exhausting temperature of 40° C., granulated for 30 minutes, divided into prescribed amounts and packaged to obtain a product. The product is a powdered juice with a fruit juice content of about 30%. The product was free of unpleasant taste and odor and stable over an extended time period.

EXAMPLE B-8
Custard cream

One hundred parts by weight of cornstarch, 100 parts by weight of a syrup containing trehalose obtained by the method in Example A-1, 80 parts by weight of maltose, 20 parts by weight of sucrose and one part by weight of sodium chloride were mixed to homogeneity, added with 280 parts by weight of egg, stirred, gradually added with 1,000 parts by weight of boiling milk, further stirred on slow fire till the cornstarch completely gelatinized and the content gave a semitransparency, after which the resultant was cooled, added with an appropriate amount of vanilla flavor, divided into prescribed portions and packaged to obtain a product. The product has a smooth gloss, mild sweetness and superior taste.

EXAMPLE B-9

"Uiro-no-moto"

Ninety parts by weight of rice powder was mixed to homogeneity with 20 parts by weight of cornstarch, 40 parts by weight of sucrose, 80 parts by weight of a crystalline trehalose hydrate powder obtained by the method in Example A-3 and 4 parts by weight of pullulan to obtain "uiro-no-moto". The uiro-no-moto was then kneaded to homogeneity with appropriate amounts of "matcha" or powdered green tea in water, placed in vessels and steamed for 60 minutes to obtain "matcha-uiro". The product is superior in gloss, texture, taste and flavor. The product has an extended shelf life because retrogradation of starch is effectively suppressed.

EXAMPLE B-10

"An (bean paste)"

In conventional manner, 10 parts by weight of adzuki bean as material was added with water and boiled and the astringency, harshness and water-soluble concomitants were removed to obtain about 21 parts by weight of a lumpy raw adzuki bean paste. The raw bean paste was then added with 14 parts by weight of sucrose, 5 parts by weight of a syrup containing trehalose obtained by the method in Example A-7 and 4 parts by weight of water, boiled, further added with a small amount of salad oil and kneaded with care of not disrupting the granules of adzuki beans, thus obtaining about 35 parts by weight of a bean paste product. The product, which is free of discoloration and superior in texture, taste and flavor, is suitable as material for "anpan", "manju", "dango", "monaka" and frozen desserts.

EXAMPLE B-11

Bun

In conventional manner, 100 parts by weight of wheat flour, 2 parts by weight of yeast, 5 parts by weight of sucrose, one part by weight of a powder with a high trehalose content obtained by the method in Example A-2 and 0.1 part by weight of inorganic foods were kneaded in water, fermented at 26° C. for 2 hours, aged for 30 minutes and baked. The product is a high-quality bun with a superior color and texture, an appropriate elasticity and a mild sweetness.

EXAMPLE B-12

Ham

One thousand parts by weight of upper parts of pig leg was uniformly salted with 15 parts by weight of sodium chloride and 3 parts by weight of potassium nitrate and piled up in chilled place for one day. The resultant was soaked in chilled place for 7 days in a salting solution consisting of 500 parts by weight of water, 100 parts by weight of sodium chloride, 3 parts by weight of potassium nitrate, 40 parts by weight of a powder with a high trehalose content obtained by the method in Example A-2 and spices, washed with chilled water, bound, smoked, cooked, cooled and packaged to obtain a product. The product is a high-quality ham with a superior color, taste and flavor.

EXAMPLE B-13

Powdered peptide

One part by weight of "HIMUTE S", a soybean peptide in 40% solution directed to use in food products commercialized by Fuji Oil Co., Ltd., Osaka, Japan, was mixed with 2 parts by weight of a high-purity crystalline trehalose hydrate obtained by the method in Example A-6, placed in plastic baths, dried at 50° C. in vacuo and cut to obtain a powder product of peptide. The product, which is superior in taste and flavor, can be favorably used as material in confectioneries such as mixes and ice desserts, as well as babies' foods and nutriment for therapeutic uses including oral and parenteral liquid foods.

EXAMPLE B-14

Powdered miso

One part by weight of red miso was mixed with 3 parts by weight of an anhydrous crystalline trehalose powder obtained by the method in Example A-4, poured in a plurality of concaves on metal plate, allowed to standing at ambient temperature overnight for solidification and put off from the plate to obtain miso solids, about 4 g each, which were then fed to cutting machine into powder. The product can be favorably used as seasoning inconvenient Chinese-style noodles and "suimono", a type of clear soup. While the miso solids can be used intact as confectionery, as well as solid seasoning.

EXAMPLE B-15

Powdered egg york

Raw egg york was pasteurized at 60°–64° C. on plate heater and the obtained egg york liquid was mixed with 4 parts by weight of an anhydrous crystalline trehalose powder obtained by the method in example A-4 against one part by weight of the egg york liquid, distributed in baths and allowed to standing overnight to convert the trehalose into crystalline hydrate form, thus obtaining solid products of block form. The solid products were then fed to cutting machine to obtain a powdered egg york. The product can be favorably used as material for confectioneries such as mixes, ice desserts and emulsifier, as well as babies' food and nutriment for therapeutic uses including oral and parenteral liquid foods.

EXAMPLE B-16

Cosmetic cream

Two parts by weight of polyoxyethylene glycol monostearate, 5 parts by weight of self-emulsifying glycerin monosterate, 2 parts by weight of a powder with a high trehalose content obtained by the method in Example A-2, one part by weight of alpha-glycosyl rutin, one part by weight of liquid paraffin, 10 parts by weight of glyceryl trioctanate and an appropriate amount of antiseptic were dissolved by heating in conventional manner, added with 2 parts by weight of L-lactic acid, 5 parts by weight of 1,3-butylene glycol and 66 parts by weight of refined water, fed to homogenizer for emulsification and admixed by stirring with an appropriate amount of flavoring agent to obtain a cream product. The product, which bears anti-oxidization activity and elevated stability, can be favorably used as high-quality anti-suntan agent, skin-refining agent and skin-whitening agent.

EXAMPLE B-17

Powdered ginseng extract

One half part by weight of ginseng extract was kneaded together with 1.5 parts by weight of an anhydrous crystalline trehalose powder obtained by the method in Example A-4, placed in baths and allowed to standing for 2 days to convert the trehalose into crystalline hydrate form, thus obtaining solid products in block form. The solid products were then fed to cutting machine for pulverization and sieved to obtain a powdered ginseng extract. The powder was fed to granulater together with appropriate amounts of vitamin B1 and vitamin B2, both in powder, into a granular ginseng extract containing vitamins. The product can be favorably used as tonic. Further the product can be also used as hair restorer.

EXAMPLE B-18

Solid agent

A natural human interferon-alpha preparation commercialized by Hayashibara Biochemical Laboratories, Inc., Okayama, Japan, was applied to an immobilized anti-human interferon-alpha antibody column in conventional manner so as to adsorb the human interferon-alpha and also to pass through the bovine serum albumin as stabilizer, and the adsorbed natural human interferon-alpha was eluted with a physiological saline containing 5% high-purity crystalline trehalose hydrate obtained by the method in Example A-6 while changing the pH level in the saline. The obtained liquid was filtered through membrane, added with about 20-fold amount of "FINETOSE", an anhydrous crystalline maltose commercialized by Hayashibara Biochemical Laboratories, Inc., Okayama, Japan, for desiccation, pulverized and fed to tabletting machine to obtain tablets, about 200 mg each, which contained about 150 units of natural human interferon-alpha per tablet. The product can be favorably used as sublingual tablet in the treatment of viral diseases, allergic diseases, rheumatism, diabetes and malignant tumors where the product is orally administered in a dose of 1–10 tablets/day/adult. Especially the product can be favorably used in the treatment of AIDS and hepatitis whose incidences have been rapidly increasing in these years. The product retains its activities over an extended time period even when allowed to standing at ambient temperature because both non-reducing saccharide according to the present invention and anhydrous crystalline maltose act as stabilizers.

EXAMPLE B-19

Sugar-coated tablet

Non-coated tablets as core material, 150 mg each, were coated with an undercoating liquid consisting of 40 parts by weight of a high-purity crystalline trehalose hydrate obtained by the method in Example A-8, 2 parts by weight of pullulan with an averaged molecular weight of 200,000 daltons, 30 parts by weight of water, 25 parts by weight of talc and 3 parts by weight of titanium oxide to give about 230 mg per tablet, further coated with a final coating liquid consisting of 65 parts by weight of the same crystalline trehalose hydrate, one part by weight of pullulan and 34 parts by weight of water and polished with liquid wax to obtain sugar-coated tablets with superior glossy appearance. The product has a superior shock resistance and retains a high-quality over an extended time period.

EXAMPLE B-20

Dentifrice

Formulation (parts by weight):

| | |
|---|---|
| Calcium hydrogen phosphate | 45.0 |
| Pullulan | 2.95 |
| Sodium lauryl sulfate | 1.5 |
| Glycerin | 20.0 |
| Polyoxyethylene sorbitan laurate | 0.5 |
| Antiseptic | 0.05 |
| Crystalline trehalose hydrate powder obtained by the method in Example A-8 | 12.0 |
| Maltitol | 5.0 |
| Water | 13.0 |

The above described materials were mixed in conventional manner to obtain a dentifrice. The product, which has an appropriate sweetness, is suitable as children' dentifrice.

EXAMPLE B-21

Solid agent for liquid food

A composition consisting of 500 parts by weight of a high-purity crystalline trehalose hydrate prepared by the method in Example A-6, 270 parts by weight of powdered egg york, 4.4 parts by weight of sodium chloride, 1.8 parts by weight of potassium chloride, 4 parts by weight of magnesium sulfate, 0.01 part by weight of thiamin, 0.1 part by weight of sodium ascorbate, 0.6 parts by weight of vitamin E acetate and 0.04 parts by weight of nicotinamide was divided into 25 g aliquots which were then packed in moisture-proof laminated bags and heat-sealed to obtain a product. One bag of the product is dissolved in about 150–300 ml water into a liquid food which is then administered in the oral or nasal cavity, stomach or intestine for energy supplement to living bodies.

EXAMPLE B-22

Infusion agent

A high-purity crystalline trehalose hydrate produced by the method in Example A-6 was dissolved in water to about 10 w/v %, passed through membrane to remove pyrogens, sterilely bottled in plastic bottles and sealed in conventional manner. The product is a stable infusion agent which is free of alteration in time course and suitable for intravenous and intraperitoneal administration. The product is isotonic at 10 w/v % to blood and therefore capable of supplementing at the concentration 2-fold more energy than in case of using glucose.

EXAMPLE B-23

Infusion agent

A high-purity crystalline trehalose hydrate obtained by the method in Example A-9 and an amino acid mixture with the below described formulation were mixed and dissolved in water to 5 w/v % and 30 w/v % respectively, purified similarly as in EXAMPLE B-22 to remove pyrogens, distributed in plastic bags and sealed.

Formulation of the amino acid mixture (mg/100 ml):

| | |
|---|---|
| L-Isoleucine | 180 |
| L-Leucine | 410 |
| L-Lysine hydrochloride | 620 |
| L-Methionine | 240 |
| L-Phenylalanine | 290 |
| L-Threonine | 180 |
| L-Tryptophane | 60 |
| L-Valine | 200 |
| L-Arginine hydrochloride | 270 |
| L-Histidine hydrochloride | 130 |
| Glycine | 340 |

The product is a stable infusion agent which is free of alteration in time course and favorably administrable through intravenous and intraperitoneal routs because trehalose exhibits no reducing power even in this type of composition of saccharide and amino acid. The procut can be favorably used to supplement both energy and amino acids to living bodies.

EXAMPLE B-24

Ointment for treating external injury

Two hundred parts by weight of a crystalline trehalose hydrate powder prepared by the method in Example A-8 and 300 parts by weight of maltose were first admixed with 3 parts by weight of iodine in 50 parts by weight of methanol, then with 200 parts by weight of 10 w/v % aqueous pullulan solution, thus obtaining an ointment with an appropriate extensibility and adhesiveness. The use of the product superiorly heals external injuries in a shortened treatment period because the iodine and trehalose in the product act as disinfectant and energy supplementing agent to viable cells respectively.

As obvious from the above, non-reducing saccharides can be very easily produced with less time from cultures by cultivating in a nutrient culture medium with maltose a microorganism capable of producing maltose/trehalose conversion enzyme, facilitating the industrial-scale production of trehalose or saccharide containing the same. The use of maltose which is obtainable by subjecting a liquefied starch to either beta-amylase or to beta-amylase and starch-debranching enzyme extremely increases the yield for trehalose from starch, facilitating much more the industrial-scale production of trehalose. The trehalose or saccharide containing the same bears a superior stability, as well as bearing a high-quality and mild sweetness. Further either of these is digested and absorbed as calorie source when orally intaken. Especially, trehalose is readily metabolized and utilized even when parenterally used. Thus the non-reducing saccharides and less reducing saccharides containing the same according to the present invention can be favorably used as sweetener, taste improving agent, quality improving agent, stabilizer and shape imparting agent in a variety of compositions including food products, cosmetics and medicines.

The present invention would open an entirely novel way to industrial-scale production to provide at low cost desired amounts of trehalose or saccharide containing the same, which have been in great demand but not easily obtained, from starch as cheap and indefinite source. Thus the effect of the present invention would come up to agricultural, fishery and stock breeding and chemical industries as well as to food, cosmetic and pharmaceutical industries and its industrial significance would be inestimatable.

We claim:

1. A process for producing trehalose comprising:
   cultivating in a nutrient culture medium with maltose a microorganism capable of producing a maltose/trehalose conversion enzyme which produces trehalose from maltose but not from sucrose; and
   collecting trehalose from the resultant culture.

2. The process of claim 1, wherein 20 w/v % or less maltose is incorporated in the nutrient culture medium.

3. The process of claim 1, wherein a surface-active agent is incorporated along with maltose in the nutrient culture medium.

4. The process of claim 1, wherein said microorganism is selected from the group consisting of microorganisms of the genus Pimelobacter, Pseudomonas and Thermus.

5. The process of claim 1, wherein the cultivation is carried out in batchwise, continuous or semicontinuous manner.

6. A process for producing trehalose comprising:
   cultivating in a nutrient culture medium containing maltose a microorganism capable of producing a maltose/trehalose conversion enzyme which enzyme produces trehalose from maltose but not from sucrose;
   adding to the culture medium glucoamylase or α-glucosidase; and
   collecting trehalose from the resultant mixture.

7. The process of claim 1 wherein said trehalose contains at least one member selected from the group consisting of glucose and maltose.

8. The process of claim 6 wherein said trehalose contains at least one member selected from the group consisting of glucose and maltose.

9. The process of claim 6 wherein said microorganism is selected from the group consisting of microorganisms of the genera Pimelobacter, Pseudomonas and Thermus.

10. A process for producing trehalose comprising: cultivating in a nutrient culture medium containing maltose a microorganism capable of producing a maltose/trehalose conversion enzyme, which enzyme produces trehalose from maltose but not from sucrose;
    collecting saccharides containing trehalose, maltose and glucose from the culture;
    adding to said saccharides glucoamylase or α-glucosidase; and
    collecting trehalose from the resultant mixture.

11. The process of claim 10 wherein said trehalose contains at least one member selected from the group consisting of glucose and maltose.

12. The process or claim 10 wherein said microorganism is selected from the group consisting of microorganisms of the genera Pimelobacter, Pseudomonas and Thermus.

* * * * *